United States Patent [19]
Patke et al.

[11] Patent Number: 5,824,062
[45] Date of Patent: Oct. 20, 1998

[54] BILEAFLET HEART VALVE HAVING DYNAMIC PIVOT MECHANISM

[75] Inventors: Nandkishor G. Patke, Shoreview; Adel A. Mikhail, Bloomington; Gene E. Stobbs, Brooklyn Park; Shelley N. Johnson, Minnetonka, all of Minn.

[73] Assignee: CV Dynamics, Inc., Inver Grove Heights, Minn.

[21] Appl. No.: 626,170

[22] Filed: Mar. 29, 1996

Related U.S. Application Data

[63] Continuation-in-part of Ser. No. 412,696, Mar. 29, 1995, abandoned, and a continuation-in-part of Ser. No. 546,210, Oct. 20, 1995, abandoned.

[51] Int. Cl.⁶ ................................................ A61F 2/24
[52] U.S. Cl. ................................................ 623/2
[58] Field of Search ................................................ 623/2

[56] References Cited

U.S. PATENT DOCUMENTS

| | | |
|---|---|---|
| Re. 31,040 | 9/1982 | Possis . |
| 3,859,668 | 1/1975 | Anderson . |
| 3,903,548 | 9/1975 | Nakib . |
| 4,078,268 | 3/1978 | Possis . |
| 4,114,202 | 9/1978 | Roy et al. . |
| 4,159,543 | 7/1979 | Carpentier . |
| 4,178,639 | 12/1979 | Bokros . |
| 4,240,161 | 12/1980 | Huffstutler, Jr. . |
| 4,276,658 | 7/1981 | Hanson et al. . |
| 4,308,624 | 1/1982 | Klawitter . |
| 4,328,592 | 5/1982 | Klawitter . |
| 4,357,715 | 11/1982 | Klawitter . |
| 4,373,216 | 2/1983 | Klawitter . |

(List continued on next page.)

FOREIGN PATENT DOCUMENTS

| | | | |
|---|---|---|---|
| 1572602-A1 | 6/1990 | U.S.S.R. . | |
| 1819588 | 6/1993 | U.S.S.R. ................ | 623/2 |
| 9108719 | 6/1991 | WIPO .................... | 623/2 |

OTHER PUBLICATIONS

Feikes, H., et al., Preservation of All Chordae Tendinae and Paillary Muscle During Mitral Valve Replacement with a Tilting Disc Valve, Journal of Cardiac Surgery, vol., No. 2 (1990).

Iung, B., et al., Small Abnormal Echos After Mitral Valve Replacement with Bileaflet Mechanical Prostheses: Predisposing Factors and Effect on Thromboembolism, J. Heart Valve Dis. vol. 2, No. 3 (May 1993).

Stoddard, M., et al., Fibrin Strands are Frequently Attached to St. Jude Medical Mitral Valve Prosthesis as Assessed by Transesophageal Echocardiography, 65th Sess. of the Am. Heart Assoc., Cir. 86 (Supp. I): I–I125 (Nov. 1992).

Brewer, L., Prosthetic Heart Valves, Chapters 19–20, pp. 285–314 (Thomas 1969).

Pierce, W., et al., A Hinged Prosthetic Cardiac Valve Fabricated of Rigid Components, J. Thoracic and Cardiovasc. Surg., vol. 56, No. 2 (1968).

Medical Incorporated brochure, Profile and Leaflet Preservation, undated.

*Primary Examiner*—David H. Willse
*Attorney, Agent, or Firm*—Robert C. Freed; Moore & Hansen

[57] ABSTRACT

A bileaflet heart valve comprising an annular base and pivoting leaflets. Each leaflet if "free-floating" within recesses without fixed rotational axis, to increase translational movement and redistribute stresses. Each recess fluidly communicates with a groove extending at least partially around the inner surface of the annular base and flow is directed through the recesses at different angles during antegrade circulation, retrograde circulation, and valve closure. A recess entrance angle to each of the recesses preferably being less than about 35° and the pivoting mechanism within the recess including first and second fulcrum edges of each leaflet shiftably engaged with side surfaces of the respective recess. The leaflets have a beveled bottom surface having two separate planar surfaces which lie at an angle to one another. In preferred embodiments, a central region of each leaflet is spaced apart from the annular base when the leaflet is in a fully closed position to minimize cavitation.

15 Claims, 24 Drawing Sheets

U.S. PATENT DOCUMENTS

| | | |
|---|---|---|
| 4,443,894 | 4/1984 | Klawitter . |
| 4,451,937 | 6/1984 | Klawitter . |
| 4,535,483 | 8/1985 | Klawitter et al. ............................ 623/2 |
| 4,535,484 | 8/1985 | Marconi ...................................... 623/2 |
| 4,676,789 | 6/1987 | Sorensen et al. ............................ 623/2 |
| 4,689,046 | 8/1987 | Bokros ........................................ 623/2 |
| 4,692,165 | 9/1987 | Bokros ........................................ 623/2 |
| 4,808,180 | 2/1989 | Johnson ...................................... 623/2 |
| 4,863,458 | 9/1989 | Bokros ........................................ 623/2 |
| 4,863,459 | 9/1989 | Olin ............................................ 623/2 |
| 4,863,467 | 9/1989 | Bokros ........................................ 623/2 |
| 4,872,875 | 10/1989 | Hwang ........................................ 623/2 |
| 4,888,010 | 12/1989 | Bokros ........................................ 623/2 |
| 4,892,540 | 1/1990 | Vallana ....................................... 623/2 |
| 4,908,028 | 3/1990 | Colon et al. ................................. 623/2 |
| 4,935,030 | 6/1990 | Alonso ........................................ 623/2 |
| 4,995,881 | 2/1991 | Knoch et al. ................................ 623/2 |
| 5,002,567 | 3/1991 | Bona et al. .................................. 623/2 |
| 5,026,391 | 6/1991 | McQueen et al. ........................... 623/2 |
| 5,061,278 | 10/1991 | Bicer ........................................... 623/2 |
| 5,064,432 | 11/1991 | Reif ............................................. 623/2 |
| 5,078,737 | 1/1992 | Bona et al. .................................. 623/2 |
| 5,078,738 | 1/1992 | Couetil ........................................ 623/2 |
| 5,080,668 | 1/1992 | Bolz et al. ................................... 623/2 |
| 5,080,669 | 1/1992 | Tascon et al. ............................... 623/2 |
| 5,108,425 | 4/1992 | Hwang ........................................ 623/2 |
| 5,116,366 | 5/1992 | Hwang ........................................ 623/2 |
| 5,116,367 | 5/1992 | Hwang et al. ............................... 623/2 |
| 5,123,918 | 6/1992 | Perrier et al. ................................ 623/2 |
| 5,123,920 | 6/1992 | Bokros ........................................ 623/2 |
| 5,137,532 | 8/1992 | Bokros et al. ............................... 623/2 |
| 5,147,390 | 9/1992 | Campbell .................................... 623/2 |
| 5,152,785 | 10/1992 | Bokros et al. ............................... 623/2 |
| 5,171,263 | 12/1992 | Boyer et al. ................................. 623/2 |
| 5,178,631 | 1/1993 | Waits .......................................... 623/2 |
| 5,178,632 | 1/1993 | Hanson ....................................... 623/2 |
| 5,192,309 | 3/1993 | Stupka et al. ................................ 623/2 |
| 5,197,980 | 3/1993 | Gorshkov et al. ........................... 623/2 |
| 5,207,707 | 5/1993 | Gourley ...................................... 623/2 |
| 5,246,453 | 9/1993 | Bokros et al. ............................... 623/2 |
| 5,314,467 | 5/1994 | Shu ............................................. 623/2 |
| 5,326,372 | 7/1994 | Mhatre et al. ............................... 623/2 |
| 5,350,421 | 9/1994 | Stupka et al. ................................ 623/2 |
| 5,354,330 | 10/1994 | Hanson et al. .............................. 623/2 |
| 5,376,111 | 12/1994 | Bokros et al. ............................... 623/2 |
| 5,522,886 | 6/1996 | Milo ............................................ 623/2 |
| 5,545,216 | 8/1996 | Bokros et al. ............................... 623/2 |

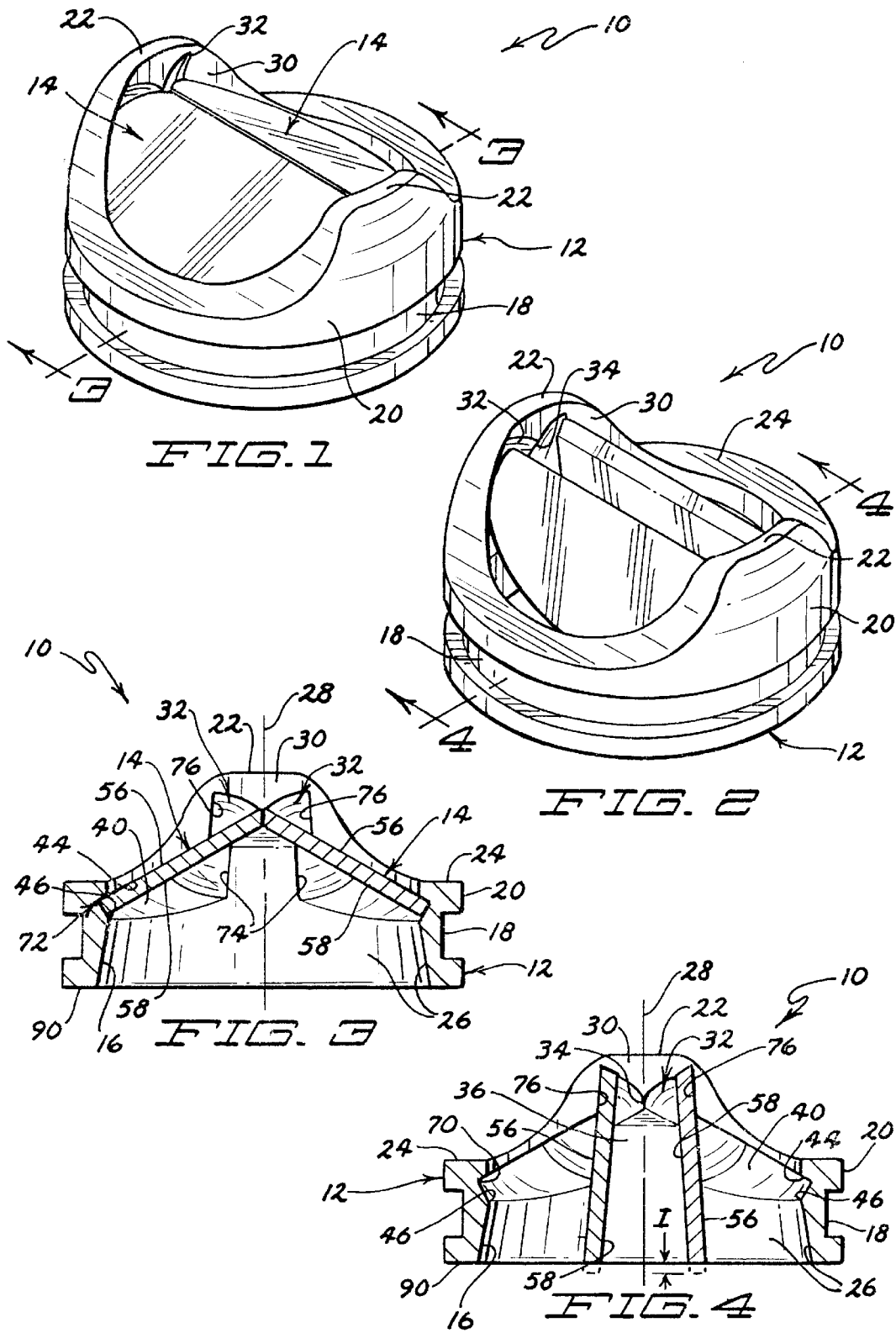

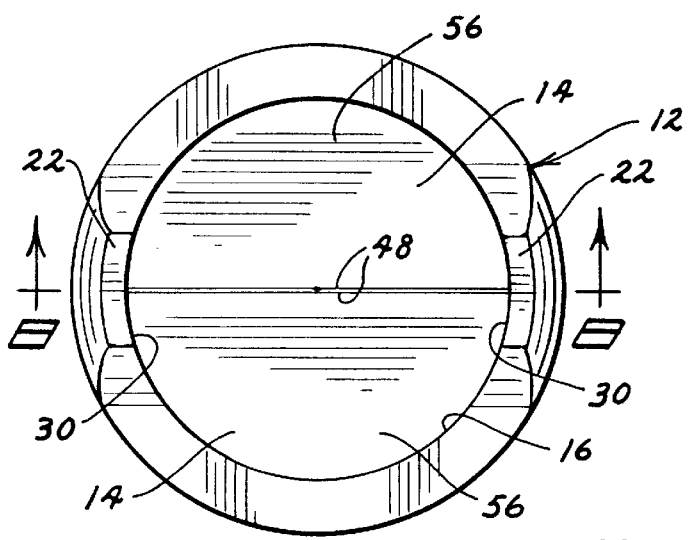
FIG. 7
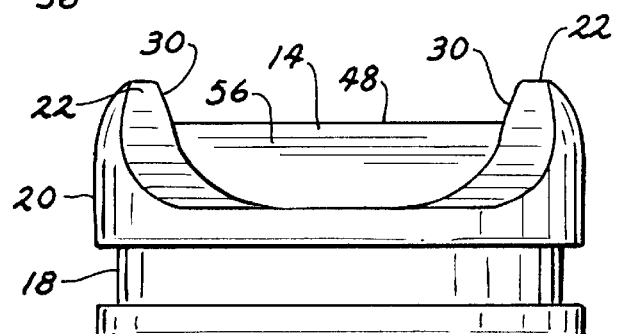
FIG. 5
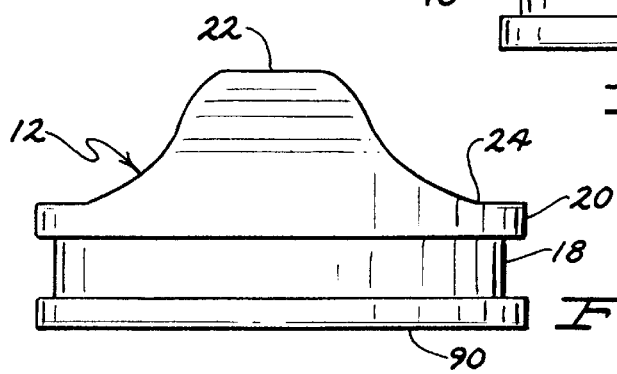
FIG. 6
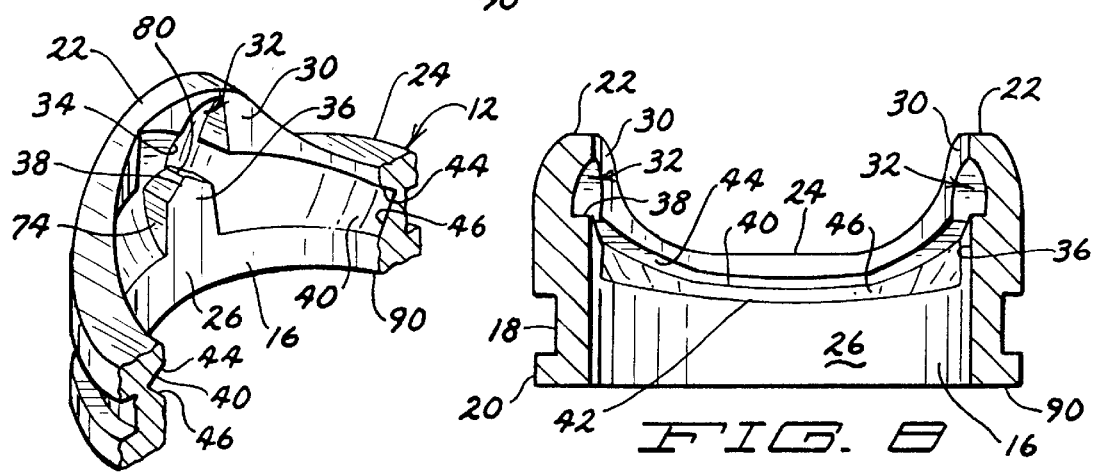
FIG. 9
FIG. 8

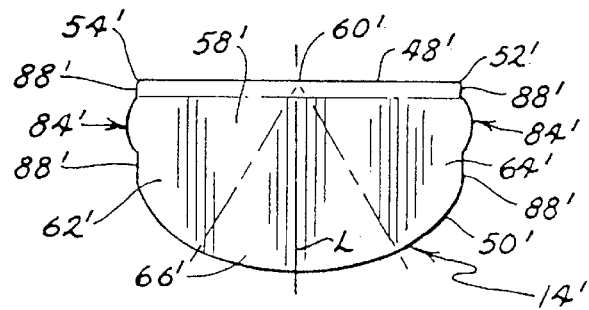
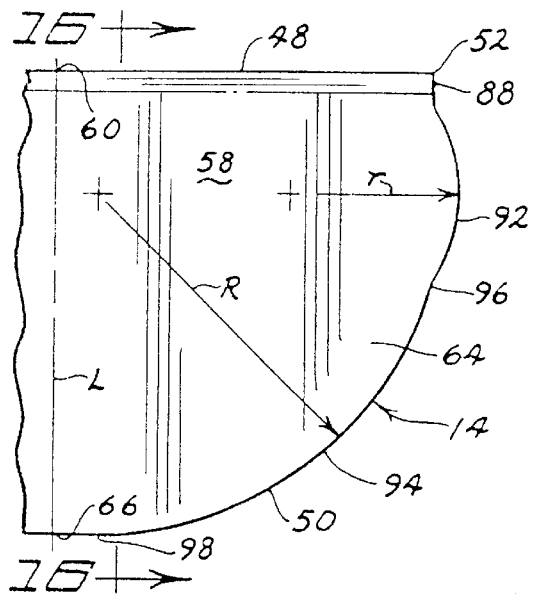
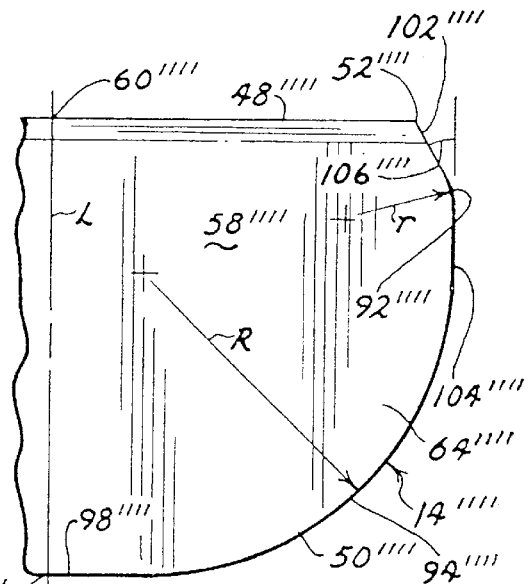
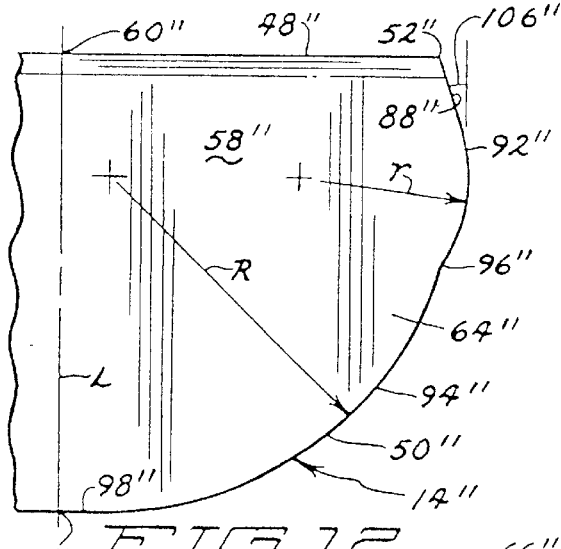
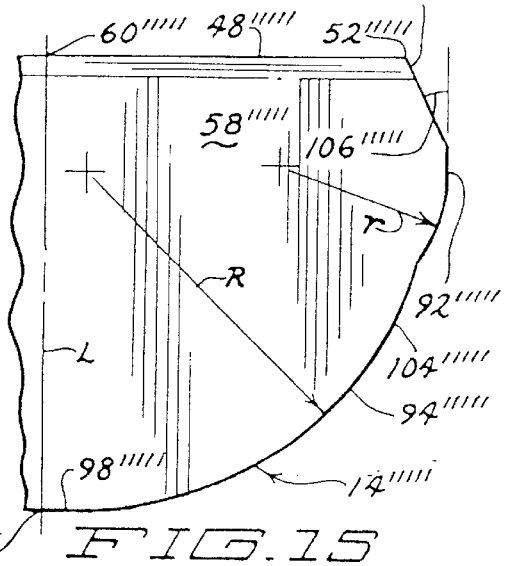

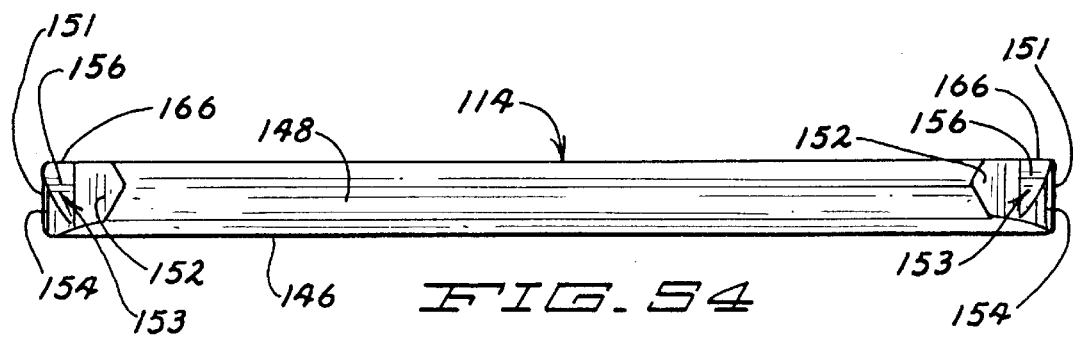
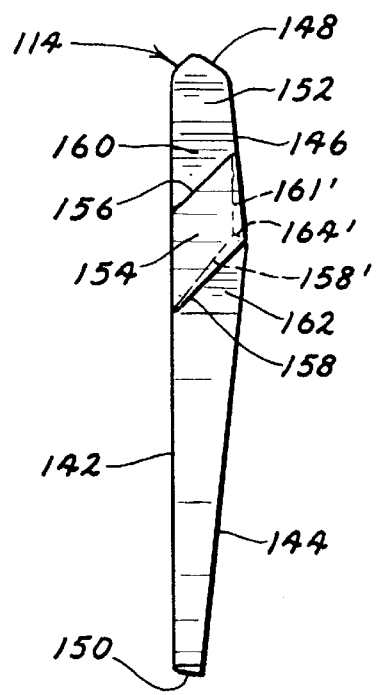
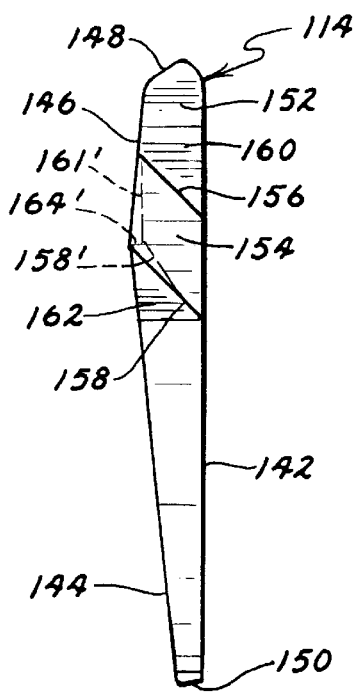
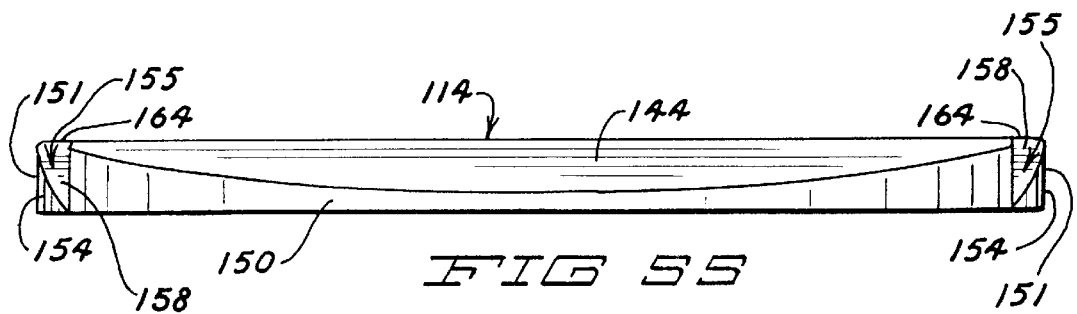

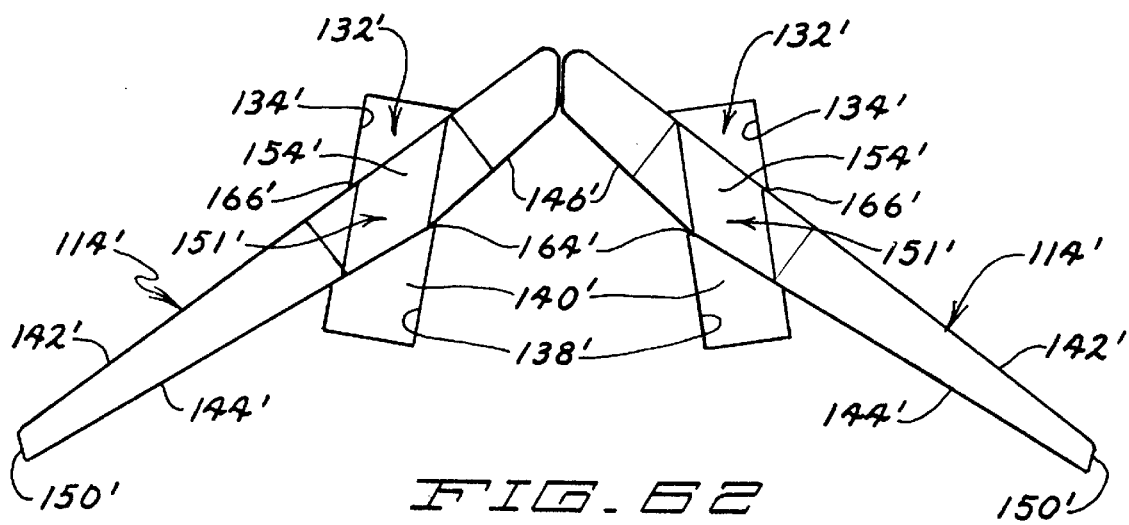
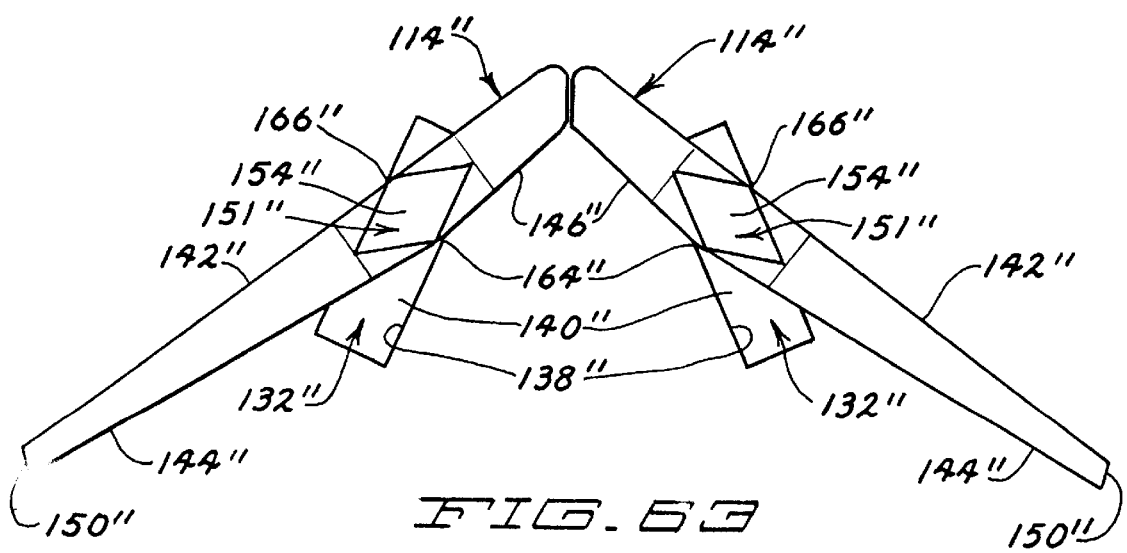

BILEAFLET HEART VALVE HAVING DYNAMIC PIVOT MECHANISM

This is a continuation-in-part of both U.S. patent application Ser. No. 08/412,696 filed Mar. 29, 1995, and now abandoned, U.S. patent application Ser. No. 08/546,210 filed Oct. 20, 1995, now abandoned, both of which have the same title as set forth above, and for which the benefit of priority is hereby claimed pursuant to 35 USC §120.

BACKGROUND OF THE INVENTION

FIELD OF THE INVENTION

This invention relates generally to bileaflet hemodynamic heart valve prostheses of the type permitting translational and rotational movement of the leaflets, and particularly to a low-excursion prosthetic heart valve suitable for mitral valve replacement involving preservation of the papillary muscle and chordal structure wherein the valve may be oriented in either an anatomical or anti-anatomical configuration.

PRIOR ART

The replacement of defective heart valves with hemodynamic prostheses is the most prevalent course of treatment for certain types of heart disease and dysfunction affecting the atrioventricular valves—namely the right AV (tricuspid) and the left AV (bicuspid) valves. Although a variety of tissue and prosthetic heart valve mechanisms have been developed, monoleaflet (tilting disc) and bileaflet valves currently hold the greatest measure of acceptance among practitioners. These valves include one or two pivoting leaflets or occluders retained within a seating collar or suture ring that is implanted in place of the physiological valve.

Replacement of a bicuspid (mitral) valve using a procedure that preserves portions of the papillary muscle and chordal apparatus is discussed herein for exemplary purposes. In that procedure, the anterior leaflet is bisected and detached from the annulus, and the two halves are groomed and then sutured to the posterior mitral annulus with the papillary muscle and chordal apparatus substantially intact. Such a procedure and its benefits are described in significant detail by H. Feikes, et al., *Preservation of All Chordae Tendineae and Papillary Muscle During Mitral Valve Replacement with a Titling Disc Valve*, 5 J. Cardiac Surg., No. 2 pp. 81–85 (1990). The authors conclude that this mitral valve replacement procedure can be practical using both monoleaflet and bileaflet valves. However, it is readily apparent to those skilled in reconstructive cardiac surgery that selection of a suitable valve type and proper orientation of the prosthesis can be important factors impacting the long term success of this procedure for a given patient. In particular, due to the position at which the valve tissue is sutured to the posterior mitral annulus, care must be taken to ensure that the peripheral edge of a leaflet does not contact the tissue during normal operation of the valve. Such contact can result in the intermittent, partial, or complete malfunction of the valve, as well as damage to or dislodgement of the valve tissue.

Four primary combinations of valve types and orientation are considered, as diagramed in FIGS. 21–24 herein. The four combinations ranked by ascending level of risk include: (1) monoleaflet valve M with anterior orientation (FIG. 21); (2) bileaflet valve with anti-anatomical orientation (FIG. 22); (3) bileaflet valve with anatomical orientation (FIG. 23); and (4) monoleaflet valve M with posterior orientation (FIG. 24). While the monoleaflet with posterior orientation is generally regarded as a high risk configuration and the monoleaflet with anterior orientation is considered to have little or no risk, the degree of risk associated with a bileaflet valve oriented in either the anatomical or anti-anatomical configuration depends upon the particular type of valve selected (particularly its range of excursions, radial exposure, and lateral exposure), the post-procedure anatomical characteristics of the annulus, and the patient's requirement for certain operational parameters associate with the valve.

While a monoleaflet valve may be preferred in order to achieve the lowest risk level with an anterior orientation, a physician may prefer to implant a bileaflet valve to obtain specific functional benefits associated with or unique to the particular bileaflet valve structure.

The bileaflet valve has been extensively developed and refined. However, there is still room for further improvement. Problems associated with the weakening or structural failure of critical components in the valve are linked both to dynamic mechanical stresses and cavitation. It is noted that a certain amount of antegrade and retrograde leakage is generally anticipated. However, the amount of leakage is preferably maintained within acceptable limits corresponding roughly to normal anatomical valves. In addition, minimizing the physical size of the valve prosthesis, particularly the longitudinal dimensions of the annular base, produces greater excursion along the peripheral edges of the leaflets, while simultaneously increasing the difficulty in raising the heights of the pivot axis. Furthermore, recesses, crevices, corners, and obstructions required to restrain the leaflets within the annular base and maintain pivotal movement also interfere with circulation, create turbulence, and produce zones of stagnation each potentially providing a thrombogenic nidus that may eventually lead to embolism. Although bileaflet valves are hemodynamic, spacing the fixed axis of rotation of the leaflets significantly apart from the secondary natural axis of rotation limits the maximum speed or angular rate which the leaflets may attain during opening and closing. There is an inherent balancing between the selection of suitable materials for ease of fabrication, biocompatibility, strength, and weight versus the acceptable level of fragility to the resulting components, particularly those involving delicate structures such as wire guides, cages, and pins that bear significant loads. In addition, the structure of many pivot mechanisms requires the annular bases to have opposing flat sides rather than a substantially or completely circular bore, thereby restricting the maximum flow volume and increasing the valve's nominal fluid pressure. Finally, although not a functional limitation, the realities of the regulatory process and competitive marketplace for prosthetic heart valves also places a burden on designers to retain some conventional features and aesthetic characteristics for purposes of FDA approval and physician acceptance.

U.S. Pat. No. 4,276,658 to Hanson provides a representative example of a conventional bileaflet heart valve. That valve utilizes a pair of semicircular pivot "ears" disposes on opposing sides of each leaflet received within "hourglass-shaped" slots to control the pivotal movement of the leaflets—including the angular sweep between the open and closed positions, the tilting of the valve away from its restrained pivotal axis, and the translational movement of the leaflet both parallel with its normal plane and along the linear flow path through the bore of the annular base. The Hanson '658 patent also describes the use of a pyrolytic carbon coating over a metallic or synthetic substrate for fabrication of the valve's components.

For comparison, U.S. Pat. Nos. 4,240,161 to Huffstutler and 3,859,668 to Anderson provide representative examples of the features, structure, and operation of monoleaflet or "titling disc" heart valves.

Various improvements directed toward correcting the deficiencies described above have been developed, each achieving varying degrees of success and accompanied by inherent tradeoffs with other beneficial features.

U.S. Pat. No. 3,903,548 to Nakib discloses an effort to utilize the beneficial features of the monoleaflet principle in a bileaflet valve that similarly omits fixed pivotal axis, however the resulting cage structure produces an unacceptably small effective bore and correspondingly high pressure gradient across the valve.

In a bileaflet valve structure such as disclosed in the Hanson '658 patent, the leaflets may each pivot fully between the open and closed portions on the order of 80,000–120,000 times per day given a standard pulse of 60–80 beats per minute. Movement of the leaflets through a viscous aerated fluid such as blood may produce significant cavitation—the formation of partial vacuums caused by sudden movement of the flowing fluid away from the surface of the leaflets as a result of mechanical forces exerted by the leaflets. These partial vacuums produce "vacuum bubbles" on or near the surface of the leaflets, and when the pressure is released, vacuums change into positive pressure regions which lead to implosion of bubbles which can cause pitting of the surface of the leaflet. The cavitation potential is amplified greatly by the virtually instantaneous stopping and starting of the leaflets as they contact a rim along the annular base and also, in the case stopping, by the rate of speed at which the leaflet is traveling when it stops. Contact between the leaflet and the rim greatly increases the compressive forces on the adjacent fluid, and as the leaflet pivots away from the rim the corresponding effects of the expansions are magnified by increased negative pressures and stronger partial vacuums. Whereas standard cavitation produces pitting of metal surfaces due only to mechanical contact between the flowing fluid and moving object, introducing reciprocal movement and mechanical contact within the fluid cause the collapsing cavitation bubbles to strip or shear material from the leaflet surfaces at an accelerated rate. Although the surface pitting occurs at a near molecular level, the result is surface degradation of the leaflet which can induce stress fractures and fragmentation leading to the premature failure of a leaflet.

U.S. Pat. No. 4,078,268 to Possis discloses a substantially circular bore through the annular base, as well as a nearly complete separation between the peripheral edges of the leaflets and the annular base around the circumference of the valve. While this design obviates certain cavitation problems, it permits high levels of antegrade and retrograde leakage and places the entire load of restraining each leaflet on a pair of pivot pins received within adjustable bearing plugs. The combination of increased torque, absorbed impact forces, vibration, and normal frictional contact are believed to exert undue mechanical stresses on the relatively delicate pivot pins and bearing plugs.

U.S. Pat. No. 5,080,669 to Tascon discloses an annular base that defines channels which intersect the pivot axis of the leaflets at various angles to direct flow of blood around enlargements in the leaflets that serve as the pivot axis, in an effort to cleanse the surfaces of the enlargements and prevent zones of thrombogenic stagnation from forming. However, the inward projections forming the channels and barriers restraining the leaflets in the Tascon '669 design create obstacles to uniform blood flow through the bore of the annular base, and define acute corners and crevices which can accelerate the formation of a thrombus. In addition, the enlargements continuously block a majority of the potential flow through each of the channels, thereby minimizing any cleansing effect that is realized.

U.S. Pat. No. 4,892,540 to Vallana discloses a pair of vertical "chimneys" defined by the lobes of the annular base and communicating with the recesses in which the ears of the respective leaflets are received. In concept, blood flow in either the antegrade or retrograde direction passes between the pivot ears and the side wall of the annular base to cleanse the recess. However, the angled base portions forming each wedge-shaped separator body hold the pivot ears and leaflets in an elevated position proximate to the inlet from the chimney into the recess, thereby minimizing flow through the chimney. The pivot ears either reduce the flow rate within the recess or divert the flow away from portions of the recess where stagnation could occur, thus diminishing the effectiveness of any cleansing action. Whereas Tascon '669 contemplates alternating between multiple flow paths oriented at diverse angles to enhance the "scrubbing" effect, Vallana '540 only contemplates cleansing that is substantially repetitive and reciprocal along one path for both antegrade and retrograde flow. Finally, to the extent that Vallana '540 would produce an acceptable retrograde cleansing action due to the pressure differential created within the recess feeding into the chimney, it is at the expense of a significantly restricted non-circular bore through the annular base accounting for a substantial reduction in antegrade circulation.

Although the Hanson '658 patent discloses the pivot ears preventing blood stagnation in the area of engagement with the recesses, the use of transesophageal echocardiography in patients receiving mitral valve replacements has shown the formation of dangling fibrin strands along the interior surface of the valve in the areas between and proximate to the pivot recesses. These small filamentous abnormal echoes (SAE) are considered non-obstructive while within the valve, however their frequent disappearance strongly suggests a thrombotic origin and a significant correlation with the risk of early thrombogenic episode has been observed.

Many factors may be responsible for the formation of the fibrin strands, including regions of blood stagnation which provide a nidus for thrombogenic formations, or defects in the materials or structure of the valve that permit the direct attachment of blood cells. It may therefore readily be appreciated that two important goals when designing a bileaflet heart valve are maintaining optimal antegrade and retrograde circulation, and eliminating regions of reduced circulation within the valve that might foster the development of a thrombogenic mass. It is suggested that while the Hanson '658 patent shows a relatively shallow semi-circular recess, in practice it has not been possible to achieve a workable commercial embodiment of a bileaflet valve having pivot ears with a suitably shallow recess to enhance cleansing of the recess by normal antegrade and retrograde circulation. For example, the commercially available embodiments of the Hanson '658 valve have recesses forming entrance angles ranging from 35° to 48° measured between the lateral wall of the bore and the tangentially adjoining surface of the recess, depending upon overall size of the valve. Recesses forming an angle of 35° or less with the adjoining lateral wall have been achieved in monoleaflet valves, however the significantly different structure and operation of monoleaflet valves has not permitted the successful utilization of many comparable features in bileaflet valves.

Various adaptations have also been made in an effort to improve the pivot mechanism. One option is to eliminate the pivot ears or pins, and allow the leaflet to rock on projections extending inwardly from the annular base. These configurations generally require some engagement between the leaflet and the projections—either the projection being received within a notch or recess in the leaflet, or the leaflet forming a trapping flange that prevents egress from between two spaced-apart projections. For example, U.S. Pat. Nos. 4,863,459 to Olin and 4,935,030 to Alonso describe leaflets that include a swelled area or camming surface trapped between two projections. U.S. Pat. Nos. 4,373,216 to Klawitter, 4,692,165 to Bokros, 4,872,875 to Hwang, and 5,354,330 to Hanson each describe a variation in which the leaflet defines a peripheral notch or recess receiving a projection the annular base. While designs utilizing a notch in the leaflet are more secure than the trapped flange configurations, they are also more difficult to assemble without placing undue stress on the leaflets or projections. In addition, these designs similarly present flat-sided bores and projections which extend into the bore and obstruct antegrade flow. As the complexity of these projections increases, the opportunity for a crevice or recess providing a thrombogenic nidus also increases. Representative examples of relatively complex pivot structures that present several potential stagnation sites include U.S. Pat. Nos. 5,116,367 to Hwang and 5,123,920 to Bokros.

One prominent feature of the bileaflet valves discussed above is the degree of exposure or incursion that is exhibited by the leaflets relative to the annular base. Excursion can be thought of as the maximum distance which the distal ends of the leaflets protrude from the bottom of the annular base when the valve is completely open, measured from the lowermost planar surface of the base to the most distal point on the peripheral edge of the respective leaflet. However, when comparing the anatomical and anti-anatomical orientation of a bileaflet valve with reference to the mitral valve replacement procedure discussed above, incursion can also encompass two more complex relationships.

It may be readily appreciated that the bileaflet valves described above have relatively large incursions, even in situations where the pivot axis have been raised into lobes extending above the top surface of the annular base. In those instances where the leaflets are retained by inward projections from the annular base or a trapping configuration, the incursion is even greater. Representative examples include the Hwang '367, Bokros '920, Olin '459, and Alonso '030 patents. If the pivotal axis of the leaflets are moved upwardly, incursions both above and below the annular base are encountered, as shown in the Bokros '165 patent.

Alternately, the overall height of the annular base can be increased rather than raising the pivotal axis on lobes, as shown in U.S. Pat. No. 5,137,532 to Bokros. However, even given the additional height of the annular base a significant incursion is still displayed.

U.S. Pat. Nos. 5,246,453 to Bokros and 5,002,567 to Bona disclose alternate configurations in which the leaflets are not generally planar, and are supported by and pivot about fulcrums disposed on the lower portion of each leaflet. While these designs present an incursion both above and below the annular base, it allows the height of the annular base to be reduced somewhat relative to comparable bileaflet valves. While such a design is considered to be more responsive to reversal in the antegrade flow, it also relies upon shifting the axis of rotation relative to the leaflet's moment of inertia and therefore produces different operational characteristics than might normally be expected.

One factor previously alluded to which affects the speed at which the valve operates, is the displacement between the fixed axis of rotation and the corresponding moment of inertia of the leaflet. Another factor is the shape of the leaflet. In this regard, optimization of several physical parameters must be contemplated. The leaflets must move through an arcuate path in response to fluid pressure applied from both the antegrade and retrograde directions, starting from differential initial orientations relative to the fluid pressure, and within an initially static versus initially dynamic environment. Consequently, valves having superior opening characteristics may be slow to close or resist complete closure, and vice versa. Leaflets having an angled, curved, or bicurved design to enhance the immediate responsiveness to changes in hemodynamic forces can be employed to address this problem. Other factors include reducing turbulence or backwash that might resist the leaflet's momentum or increase its apparent resting inertia, reducing the weight or thickness of the leaflet, allowing the leaflet to rock or cam differently in response to antegrade or retrograde pressures, maximizing the laminar flow through the valve body over the entire leaflet surface, and eliminating sources of friction, vibration, or misalignment that could adversely affect the mechanical operation of the valve.

Another approach mentioned above is to increase the translational movement of the leaflet within the annular body, thereby permitting the leaflet to pivot more naturally about its inertial axis in direct response to the hemodynamic forces. This approach can potentially be more beneficial than merely moving the fixed axis of rotation nearer to the moment of inertia, since it also serves to reduce frictional forces and other physical impediments to proper valve operation. One limitation is the need to maintain proper alignment and seating of the leaflet without encumbering the flow passage with obstructions or incorporating fragile structures that increase the likelihood of valve failure.

U.S. Pat. No. 4,535,484 to Marconi describes a bileaflet valve in which the leaflets are "free-floating", thereby increasing translational movement and reducing the mechanical stresses imposed at localized pivot points and other load bearing surfaces. However, the Marconi '484 design requires a complex and fragile cage structure to restrain the leaflets, thereby producing a significant risk of damage to the valve during manufacturing or handling and increasing the potential for catastrophic failure of a valve component that would result in death or severe injury to the patient, mitigating against the use of certain materials such as pyrolytic carbon, and greatly increasing the cost and complexity of fabrication.

For comparison, U.S. Pat. No. 4,689,046 to Bokros describes a trapezoidal pivot ear having beveled edges, arguably decreasing the translational freedom, but enhancing the "sweeping" effect of the pivot ear to prevent thrombogenic formations within the recesses and distributing lateral stresses over a wider surface area.

It may also be appreciated from analyzing bileaflet heart valves, such as disclosed by the Hanson '658 and Possis '268 patents that the leaflets divide the bore into three passages having unequal cross-sectional areas, and that corresponding effects on fluid dynamics should be expected. Observation of these valves in operation shows that flow rates through the passages will vary generally inversely with the corresponding cross-sectional area. As such, in a valve such as Hanson '658 which present a relatively narrow central passage, the flow rate of blood passing through that central passage is greater than through the two passages on opposing sides. The faster blood flow in the center, relative to the sides, can cause additional turbulence within or downstream of the valve, or produce a pressure differential or venturi effect within the valve that can impede or retard the optimal translational or pivotal movement of the leaflets. The Possis '268 valve presents a larger central passage with narrower cross-sectional passages on each side, thereby reversing the fluid dynamics compared with the Hanson '658 design.

While many common functional goals have been recognized among designers of bileaflet heart valve prostheses, there are strongly divergent opinions concerning the prioritization of those goals and how best to achieve specific results or advantages. Accordingly it will be readily appreciated that these competing factors significantly influence the design and optimization of all bileaflet heart valves and that further improvements may be made. The present invention provides advantages over the prior art bileaflet heart valves and solves problems associated therewith.

SUMMARY OF THE INVENTION

Briefly described, the bileaflet heart valve prosthesis of the present invention comprises an annular base defining a substantially circular bore, and a pair of pivoting leaflets. Each leaflet presents a substantially uniform peripheral edge without pivot ears, pins, or other fixed axis of rotation, thereby distributing mechanical stresses over a larger area of the peripheral edge. In preferred embodiments the leaflets have a beveled bottom surface which minimizes the travel angle between the open and closed positions. The lateral ends of each leaflet are received within recesses where the ends are "free floating". In preferred embodiments, each recess communicates with at least one groove extending around an inner peripheral surface of the annular base, and a cleansing flow is directed vertically or angularly through the recess to the groove during antegrade circulation, and from the grooves through the recess during retrograde flow and valve closure. The angle of this cleansing flow through the recesses varies depending upon the direction of circulation and the orientation of the leaflets, and is mostly unobstructed within the recesses by the leaflets. The peripheral edges of the leaflets present minimal incursion or exposure beneath the bottom of the annular base when the valve is completely open. When the leaflets of the valve are closed, the peripheral edge of each leaflet in the central region is preferably spaced apart from the annular base to minimize cavitation potential. The peripheral edge of each leaflet in preferred embodiments only contacts the annular base adjacent the groove proximate the lateral regions of the leaflet.

In preferred embodiments, the angle at which fluid washing the surfaces of the annular base flows into the recesses is less than 35' to permit better washing dynamics. The preferred valve also has a dynamic pivot constructed primarily on the lateral sides of the leaflets where two fulcrum edges are created by notches in the peripheral edge. The leaflets pivot on each of the respective fulcrum edges at different points in the opening and closing cycle of the valve. This mechanism also permits significant translational movement of the leaflets especially in the fully open position. This mechanism is believed to provide a pivot mechanism which permits the valve to open and close more rapidly than prior art bileaflet valves.

It is one object of this invention to design a bileaflet heart valve prosthesis of the type used for tricuspid or bicuspid (mitral) valve replacement, and particularly one which provides superior operating capabilities and minimizes the risk to the patient when implanted using a procedure involving preservation of the papillary muscle and chordal structure by fixation to the posterior mitral annulus.

It is a related object of this invention to design the above bileaflet valve for implantation in either the anatomical or anti-anatomical configuration, such that the peripheral edges of the leaflets present an extremely low incursion below the bottom surface of the annular base, and further present minimal radial and lateral exposure.

It is an additional object of this invention to design the above bileaflet valve such that the passages through the bore of the valve between the leaflets provide substantially equal relative flow rates, thereby mitigating against flow differentials, gradients, or venturi effects which would otherwise cause turbulence or impede the translational or pivotal movement of the leaflets.

It is another object of this invention to design the present bileaflet valve such that it utilizes a "free floating leaflet" configuration with no pivot ears or projections, to thereby reduce and redistribute mechanical or contact stresses otherwise focused on these pivot axis in conventional bileaflet valves.

It is a further object of this invention to design the above bileaflet valve such that it defines a cleansing channel or recess within the annular base in the region traversed by the lateral ends of the leaflets, and such that the cleansing channel is unobstructed within that region, and induces or "steers" both vertical and angular fluid flow through that region during antegrade and retrograde circulation.

It is another object of this invention to provide a bileaflet valve such that a shallow angle of less than about 35° may be formed between the lateral surfaces of the annular bore and the adjoining surfaces of the recesses which restrain the leaflets. It is believed that this will enhance cleansing of the recesses by normal antegrade and retrograde circulation.

It is a further object of this invention to provide a bileaflet valve such that the peripheral edge of each leaflet is received within a recess and beneath a seat defined by the annular base, such that there are no observable gaps between the annular base and peripheral edge in the contact regions between the leaflets and annular base when viewed from a perspective along the longitudinal axis of the valve, but wherein cavitation potential is minimized or eliminated along the central portion of the peripheral edge of the leaflet.

It is a further object of this invention to provide a bileaflet valve such that the height of the pivot axis is raised and the height of the corresponding lobes may be reduced while achieving the advantages of minimal excursion and exposures.

It is a further object of this invention to design the above bileaflet valve such that the annular base of the valve defines beveled arcuate surfaces which contact the edges of the leaflets as the leaflets move between the open and closed positions, thereby creating a generally smooth and continuous arcuate path along which the leaflets roll when pivoting between the open and closed positions to distribute stress forces over an extended region of the leaflet and annular base.

The above-described features, advantages and objects, along with various other advantages and features of novelty are pointed out with particularity in the claims of the present invention annexed hereto and forming a part thereof. However, for a better understanding of the invention, its advantages, and objects attained by its use, reference should be made to the drawings which form a further part hereof and to the accompanying descriptive matter in which there is illustrated and described preferred embodiments of the present invention.

BRIEF DESCRIPTION OF THE DRAWINGS

In the drawings, in which like and primed reference numerals indicate corresponding parts throughout the several views;

FIG. 1 is a perspective view of a bileaflet heart valve of the present invention in a completely closed position;

FIG. 2 is a perspective view of the bileaflet heart valve of FIG. 1 in a completely open position;

FIG. 3 is a cross-sectional view of the bileaflet heart valve of FIG. 1 taken through line 3—3 in FIG. 1;

FIG. 4 is a cross-sectional view of the bileaflet heart valve of FIG. 1 taken through line 4—4 in FIG. 2;

FIG. 5 is a lateral side elevation view of the bileaflet heart valve of FIG. 1;

FIG. 6 is a lateral side elevation view of the bileaflet heart valve of FIG. 1;

FIG. 7 is a top plan view of the bileaflet heart valve of FIG. 1;

FIG. 8 is a transverse cross-sectional view of the annular base of the bileaflet heart valve of FIG. 7 taken through line 8—8 in FIG. 7;

FIG. 9 is a partially broken away lateral perspective view of the annular base of the bileaflet heart valve of FIG. 7;

FIG. 10 is a bottom plan view of a prior art leaflet having semicircular pivot ears for a bileaflet heart valve;

FIG. 11 is a partially broken away bottom plan view of the leaflet shown in FIGS. 1–9;

FIG. 12 is a partially broken away bottom plan view of a first alternate embodiment of the leaflet shown in FIG. 11;

FIG. 14 is a partially broken away bottom plan view of a third alternate embodiment of the leaflet shown in FIG. 11;

FIG. 15 is a partially broken away bottom plan view of a forth alternate embodiment of the leaflet shown in FIG. 11;

FIG. 29 is a perspective view of a bileaflet heart valve of the present invention implanted in an anatomical orientation;

FIG. 52 is a vertical side view of a first lateral side of the leaflet of the preferred bileaflet heart valve shown in FIG. 42;

FIG. 53 is a vertical side view of a second lateral side of the leaflet of the preferred bileaflet heart valve shown in FIG. 42;

FIG. 54 is a horizontal side view of an upper edge, including the mating edge, of a leaflet of the preferred bileaflet heart valve shown in FIG. 42;

FIG. 55 is a horizontal bottom view of the peripheral edge of the leaflet of the preferred bileaflet heart valve shown in FIG. 42;

FIG. 62 is a diagrammatic drawing of an alternate valve having alternate recesses and an alternate relationship between the leaflets and the diamond surfaces on the lateral sides of the leaflets;

FIG. 63 is a diagrammatic drawing of another alternate valve having alternate recesses and yet another alternate relationship between the leaflets and the diamond surfaces on the lateral sides of the leaflets;

DETAILED DESCRIPTION OF THE PREFERRED EMBODIMENTS

Figure 66:
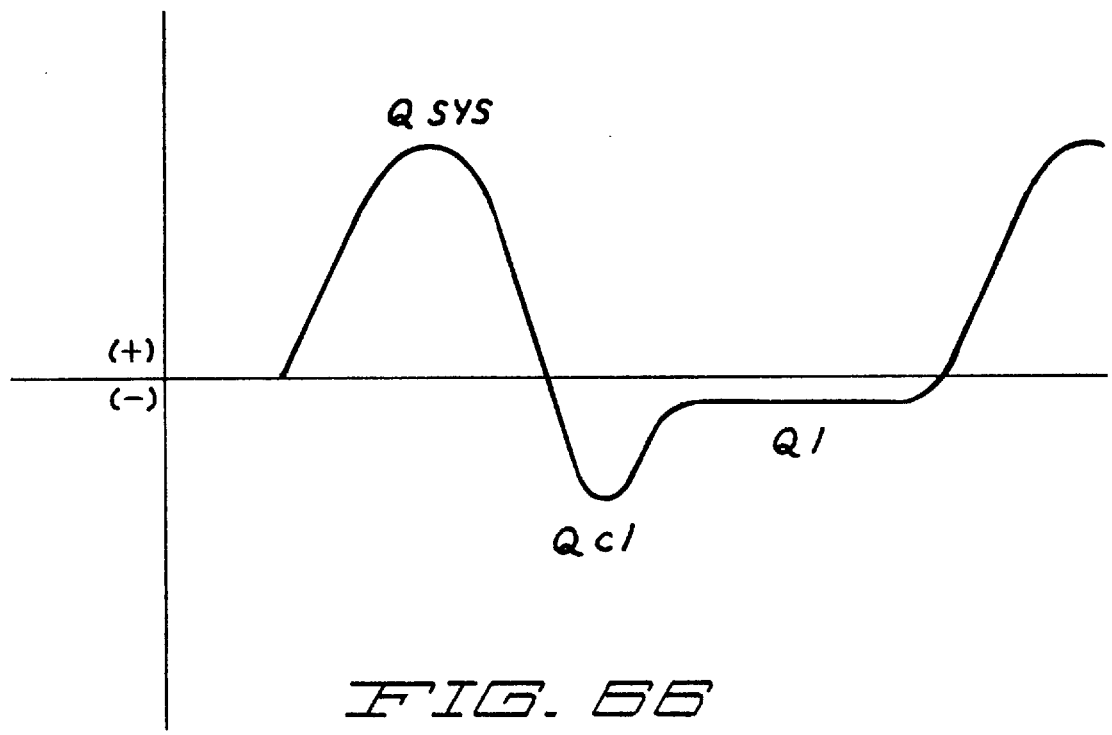
FIG. 66 provides a graphic representation of the quantity of blood flowing through a bileaflet heart valve during a single heart contraction cycle wherein the positive quantity indicates blood flowing in an antegrade direction and the negative quantity below the "y" axis indicates the quantity of blood flowing in the retrograde direction.
Figure 67:
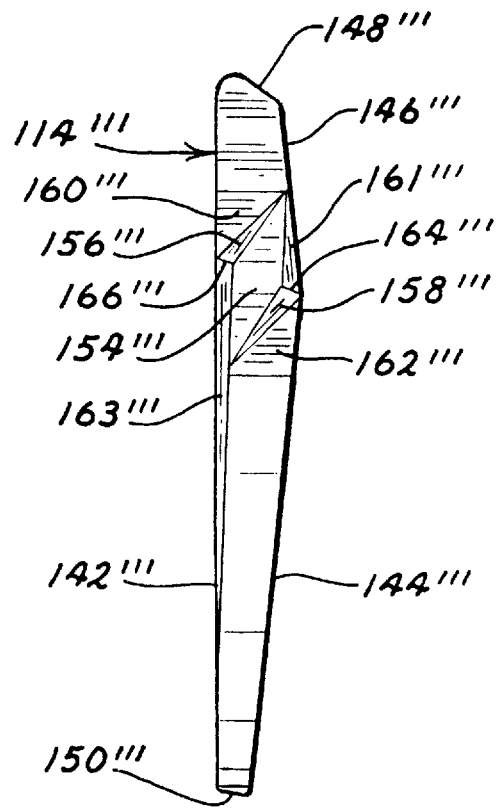
FIG. 67 is a vertical side view of a first lateral side of an alternate leaflet similar to that shown in FIG. 52, except that the alternate leaflet has beveled edges to create further surfaces so as to mate with the edges 134' and 138' of the recess 132' shown in phantom in FIG. 48.

Bileaflet heart valve prostheses of the present invention are illustrated in FIGS. 1–67 of the present application and referenced generally by the numerals 10 and 110. A number of embodiments are disclosed, the most preferred of which are disclosed in FIGS. 42–67. The description of the most preferred embodiments follows the detailed description of prior embodiments presented immediately hereinbelow.

Referring now to FIGS. 1–9, the valve 10 generally includes an annular base 12 and a pair of leaflets 14 received within the annular base and generally pivotable between a closed position, shown in FIGS. 1 and 3, and an open position, shown in FIGS. 2 and 4.

The annular base 12 defines a generally circular bore 16 extending entirely through the base 12, and a groove 18 circumscribing the generally cylindrical exterior surface 20 of the base 12 such that the valve 10 may be mounted within a suture ring (not shown) and rotate therein in a manner that is well known to the art. The groove 18 preferably has a generally u-shaped cross-section as shown in FIGS. 3 and 4.

The annular base 12 includes an inner wall 26 defining the bore 16, and a pair of lobes 22 extending above a top surface 24 of the annular base 12 proximate a midline of the valve 10 shown in FIG. 2. The inner wall 26 may be tapered or angled radially outward as much as approximately 10° relative to a longitudinal axis 28 of the valve 10 shown in FIGS. 3 and 4, or may be generally vertical as shown in FIGS. 8 and 9. The longitudinal axis 28 of the valve 10 generally approximates the linear flow path through the bore 16.

The lobes 22 of the annular base 12 are spaced apart on the diametrically opposing lateral sides of the valve 10. The inner wall 26 of the annular base 12 and the inner surfaces 30 of the lobes 22 define a pair of recesses 32 extending radially outward from the bore 16. Each recess 32 is divided into two halves, each half corresponding to one of the two leaflets 14. As may be seen in FIGS. 2, 4, 8, and 9, the adjacent halves of each recess 32 are divided by a center line 34. The annular base 12 includes a separator body 36 disposed between each half of each recess 32 and defining, in some embodiments, a generally triangular or pyramidal top.

Referring again to FIGS. 3, 4, 8, and 9, the annular base 12 further defines an interior groove 40 extending from and fluidly communicating with the lower portion of each half of the recesses 32 around the circumference of the inner wall 26 of the annular base 12, thereby defining a continuous passage extending around the periphery of circumference of the bore 16. Referring specifically to FIG. 8, the interior groove 40 has a minimum height at the central locations 42 disposed between and most distantly from the recesses 32 or lateral sides of the annular base 12, within two opposing regions that may be referred to as the lateral sides of the annular base 12. The two lateral sides of the annular base 12 are therefore oriented at right angles to the two lateral sides of the annular base, and divide the valve 10 and annular base into four equal quadrants.

The interior groove 40 flares or tapers upwardly along its top edge or surface 44 to increase the height of the groove 40 as the groove 40 traverses the inner wall 26 toward the recesses 32, such that the groove 40 has a height approximately equal to the height of the separator body 36 where the top edge 44 of the groove 40 intersects the adjacent recess 32. The bottom edge or surface 46 of the groove 40 remains generally horizontal throughout the lateral side of the annular base 12, and remains generally horizontal or tapers upward only slightly as the groove 40 traverses from the lateral side to the lateral side of the annular base 12 and intersects the bottom edge of the separator body 36. The bottom edge 46 of the groove 40 intersects the separator body 36 at a point where the inner face of the separator body 36, the innermost bottom edge 46 of the groove 40, and the inner wall 26 of the annular base 12 remain flush or coplanar with one another. Similarly, the top edge 44 of the groove remains flush or coplanar with the inner surface 30 of the lobe 22 where the top edge 44 of the groove 40 intersects the recess 32.

Figure 16:
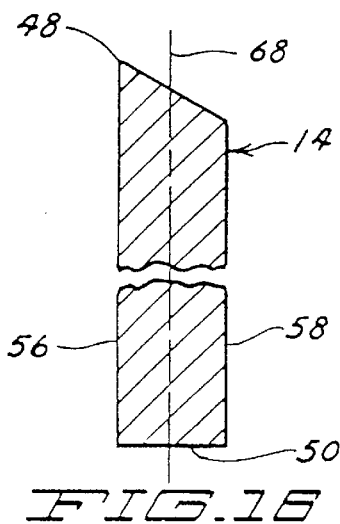
FIG. 16 is a cross-sectional view of the leaflet of FIG. 11 taken through line 16—16 in FIG. 11.

As further described in detail below, the opposing ends of a leaflet 14 are received within the corresponding and aligned halves of the two recesses 32 on each of the lobes 22, and pivot freely within the recesses 32 between the closed and open positions. Referring now to FIGS. 11 and 16, leaflets 14 generally have a straight mating edge 48, curved peripheral edge 50 extending from and between one opposing end 52 of the straight mating edge 48 to the other opposing end (not shown), a top planar surface 56 and a bottom planar surface 58. Referring now also to FIGS. 10 and 12–15, the prior art leaflet 14', shown in FIG. 10, and each of the alternate leaflets 14", 14'", 14"", and 14""', shown in FIGS. 12, 13, 14 and 15, respectively, have the same general elements as leaflet 14. These corresponding elements are shown best in FIG. 13 which illustrates a plan view of a second alternate embodiment of the leaflet 14 of FIG. 11. Leaflet 14'", illustrated in FIG. 13, has a center point 60'" along the straight mating edge 48'". From the center point 60'" along the mating edge 48'" of each spaced equidistantly from the respective opposing ends 52'", 54'", the leaflet 14'" may be divided into three equiangular regions including a first lateral portion 62'", a second lateral portion 64'", and a central portion 66'" disposed between the first and second lateral portions 62'", 64'", respectively. The corresponding first and second lateral portions 62'", 64'" of each leaflet defines and encompasses the opposing lateral ends of each leaflet 14', 14", 14'", 14"", 14""'. The alternate leaflet 14'" also defines a longitudinal or planar axis 68'" oriented generally parallel to the top and bottom planar surfaces 56'", 58'".

Referring again to FIGS. 3, 4, 8, 9 and 11, it will be appreciated that the surfaces defining the top and bottom of the interior groove 40 extend from the corresponding top edge 44 and bottom edge 46 adjacent the inner wall 26 outwardly to converge at a radial vertex 70 forming a generally right angle therebetween in the proximity of the vertex 70. The top surface and bottom surface of the groove 40 are therefore oriented such that the peripheral edge 50 of the corresponding leaflet 14 does not contact the bottom surface or bottom edge 46 of the groove 40 as the leaflet 14 pivots through an arc from the closed position to the open position.

Correspondingly, sufficient clearance is also provided between the lower surface and lower edge 46 and the peripheral edge 50 of the leaflet 14 to permit translational movement of the leaflet 14 along its planar axis 68. As such the bottom surface of the groove 40 is preferably curved or arcuate to mirror the maximum arc transcribed by the peripheral edge 50 of the leaflet 14. Similarly, it may be appreciated that the top surface 44 of the interior groove 40 is oriented such that it is generally parallel to and coplanar with the top surface 56 of the leaflet 14 along the peripheral edge 50 of the leaflet 14 when the leaflet 14 pivots to the fully closed position as shown in FIG. 3, and may therefore be substantially planar between the vertex 70 and junction between the top edge 44 and side wall 26.

The top edge or surface 44 of the interior groove 40 forms a stop or seating surface against which the top planar surface 56 of the leaflet 14 rests to prevent retrograde flow through the bore 16 of the valve 10. However, as previously described, reciprocal movement and mechanical contact between the leaflet 14 and annular base 12 accelerates the structural degradation and weakening of the leaflet 14 cause by cavitation forces.

To reduce the potential for deleterious cavitation effects, the top planar surface 56 and peripheral edge 50 of the leaflet 14 is disposed or spaced-apart a distance from the top planar surface 44 of the interior groove 40 along at least the central portion 66 or region of the leaflet 14. This may be accomplished in any one of a number of ways.

First, the radius of the peripheral edge 50 of the leaflets 14 maybe foreshortened within the central region 66 of the leaflet 14, thereby preventing contact between the leaflet 14 and annular base 12 in that region 66, but also permitting increased retrograde leakage through the separation or gap 72 that is formed.

A second method is to curve the top surface and top edge 44 of the interior groove 40 upwardly as the top edge 44 approaches the lateral sides of the annular base 12 and recesses 32, thereby limiting contact between the leaflets 14 and annular base 12 to within the lateral side regions 62, 64 of the leaflets 14. Although contact between the lateral side regions 62, 64 of the leaflet 14 and the annular base 12 may induce some cavitation, it is contained within regions 62, 64 of the leaflet 14 where the linear or angular speed of the peripheral edge 50 of the leaflet 14 through the fluid is significantly slower than in the central region 66. Since the most deleterious cavitation effects are proportionally related to the relative speed of the leaflet 14 through the fluid medium, and this relationship is not linear around the peripheral edge 50 of leaflet 14, the result is to diminish a substantial proportion of the cavitation effects induced for the entire leaflet 14 by eliminating contact between the leaflet 14 and annular base 12 along approximately one third of the peripheral edge 50 of the leaflet 14.

These two methods will reduce the speed of the leaflet 14 as it closes. As the edge 50 of the leaflet 14 approaches surface 40 of the base 12, the decreasing gap 72 offers increased resistance to the fluid that squeezes through the gap 72. This resistance to "squeezed flow" results in reduced speed of the leaflet 14 at closing.

A third method is to restrict contact between the leaflet 14 and the annular base 12 to the surfaces of the recesses 32 and separator body 36. This method reduces the effects of reciprocal movement and contact along substantially all of the entire peripheral edge 50, except the regions of the lateral sides 62, 64 forming the pivotal contacts within the recesses 32, where cavitation effects are at a minimum due to the relatively slow movement of the leaflet 14 through the fluid medium, and tangential contact does not significantly magnify those effects. This method also focuses additional mechanical stresses on the lateral sides 62, 64 and peripheral edge 50 of the leaflet 14 in the areas directly adjacent to the pivot axis. The linear speed of the leaflets 14 is not diminished since there is no area to cause the resistance or "squeezed flow." Consequently, the advantage of redistributing mechanical stresses created by restraining the pivotal movement of the leaflet 14 over a larger area of the peripheral edge 50 must be balanced against the benefits of reducing deleterious cavitation effects along a segment of the peripheral edge 50.

A fourth manner to prevent seat contact between the top surface 56 and peripheral edge 50 of the leaflet 14 and the annular base 12 would be to place discrete downward projections (not shown) along the top surface of the interior groove 40 against which the top planar surface 56 of the leaflet 14 would impinge. However, it is believed this method could focus cavitation forces at contact points along the surface 56 to peripheral edge 50 of the leaflet 14 corresponding to the locations of the projections, and lead to the creation of deeper structural fault lines within the leaflet 14 radiating from the contact points between the leaflet 14 and projections.

It will be appreciated that the separation or gap 72 formed between the peripheral edge 50 of the leaflet 14 and the annular base 12 will permit some retrograde leakage. The flow rate and volume of that leakage is reduced (1) by having the peripheral edge 50 of the leaflet 14 remain in close proximity to the bottom surface of the interior groove 40, and (2) by receiving the peripheral edge 50 of the leaflet 14 within the interior groove 40 beneath a seating surface defined by the annular base 12, such that there are little or no observable spaces or openings between the side wall 26 of the annular base 12 and the peripheral edge 50 of the leaflet 14 when viewed from a perspective along the longitudinal axis 28 of the valve.

As previously discussed, the pivotal movement of the leaflets 14 are at least in part constrained against movement by contact between the top and bottom surfaces 56, 58 of the leaflet 14 and portions of the recesses 32 and separator body 36. In particular, in the fully closed position the mating edges 48 of the leaflets 14 are disposed closely confronting or contacting one another, with upward movement of the leaflets 14 due to retrograde pressure adjacent the mating edges 48 being restrained by contact between the top surface 56 of the leaflet 14 and the top edge 44 of the interior groove 40 at the junction between the interior groove 40 and recess 32. Upward movement of the leaflets 14 along the lateral sides of the annular base 12 is also restrained by the top edge 44 of the interior groove 40, except in the central region 66 where the separation or gap 72 is maintained to reduce the effects of cavitation.

When in the fully open position as shown in FIG. 4, the bottom surface 58 of the leaflets 14 contact the tapered opposing sides 74 of the separator body 36, and the top surfaces 56 of the leaflets 14 adjacent the mating edges 48 contact the outer planar walls 76 of the recesses 32. As such, the tapered opposing sides 74 of the separator body 36 and outer planar walls 76 of the recesses 32 hold the leaflets 14 in position at a slightly acute angle relative to the longitudinal axis 28 and one another, thus preventing over-rotation of the leaflets 14 to a parallel position in which pressure exerted by retrograde circulation could be insufficient to initiate closure of the valve 10.

Figure 28:
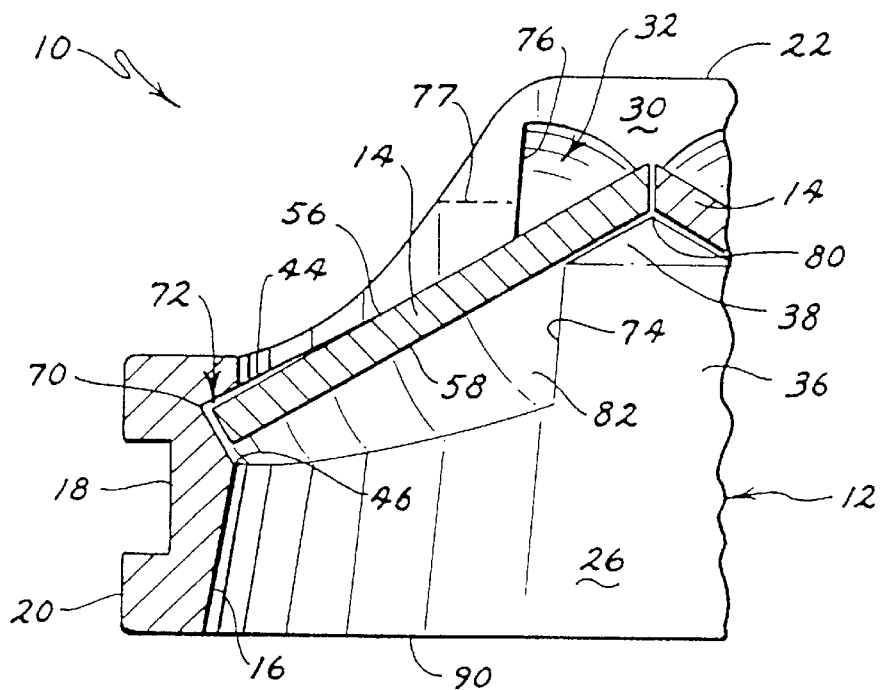
FIG. 28 is an enlarged partially broken away detailed cross-sectional view of the embodiment of the bileaflet heart valve of FIG. 3.

As such, it may be appreciated that a top segment of each lobe 22 may be removed, or reduced in the area directly adjacent the recesses, without diminishing the operation of the valve 10. In addition, the top surface of the lobe 22 may be opened to fluid communication with the recesses 32 by the removal of material forming the lobe 22 along the inner surface 30 of the lobe 22. The top segment of the lobe 22 along the inner surface 30 may be removed down to a point at or slightly above a horizontal plane defined by the peaks or apexes 80 of the separator bodies 36. This segment is denoted by the horizontal phantom line 77 in FIG. 28. Top surfaces 38 of the separator body 36, as well as the outer planar walls 76 of the recesses 32, may also be beveled, tapered, or angled slightly in alternate embodiments relative to the orientation shown. In alternate embodiments shown in FIGS. 34, 37, 38 and 41, surfaces which generally correspond to these surfaces are beveled.

Translational movement of the leaflets 14 is restrained by contact between the peripheral edge 50 of each leaflet 14 along a limited zone within the lateral side regions 62, 64 and the confronting curved radial surfaces of the recesses 32.

Figure 25:
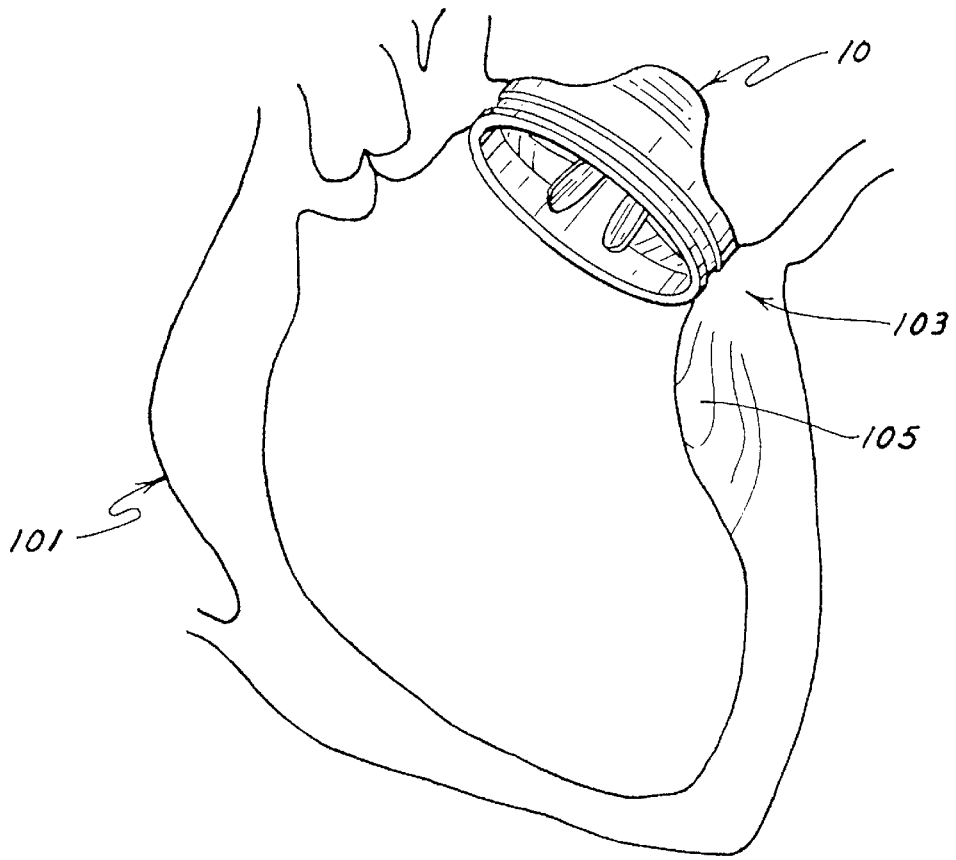
FIG. 25 is a diagrammatic view of a prior art leaflet and recess having a semi-circular pivot ear.
Figure 25:
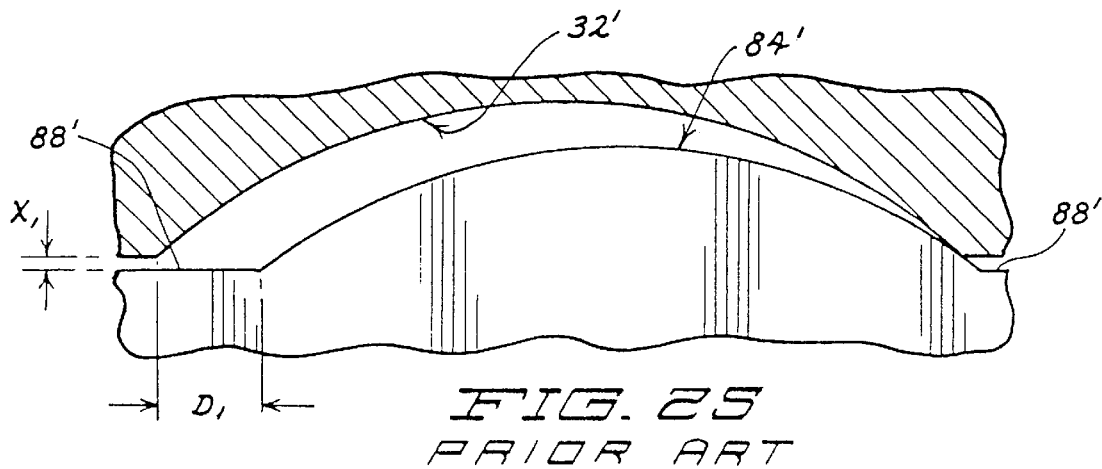
Figure 26:
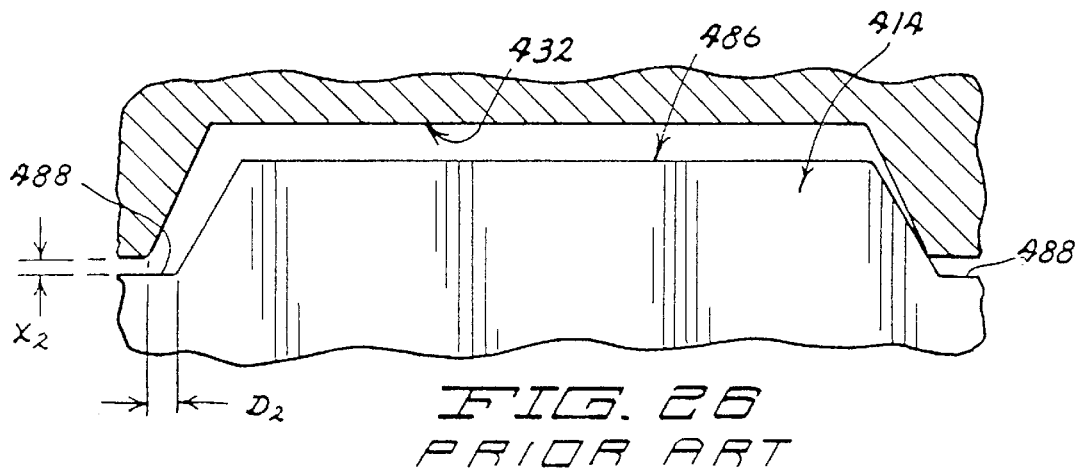
FIG. 26 is a diagrammatic view of a prior art leaflet and recess having a trapezoidal pivot ear.
Figure 27:
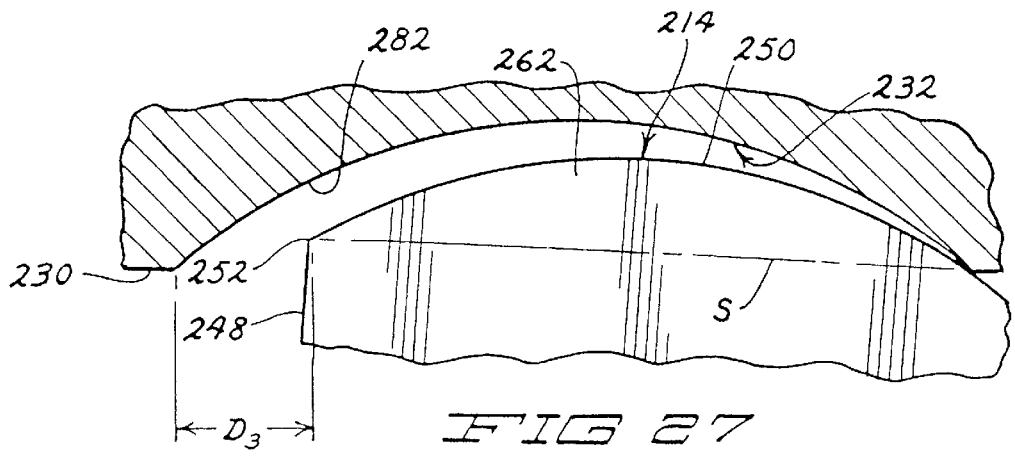
FIG. 27 is a diagrammatic view of a earless leaflet and recess of this invention.
Figure 30:
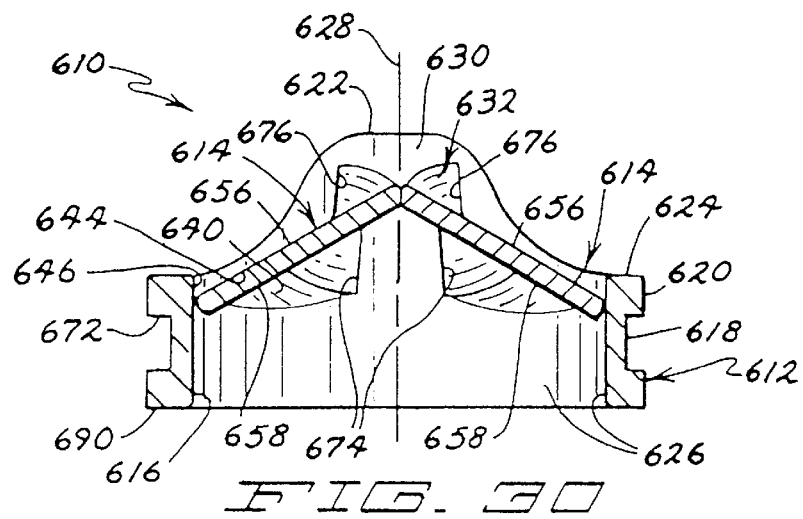
FIG. 30 is a cross-sectional view of an alternate embodiment of the bileaflet heart valve of FIG. 1 showing the leaflets in the closed position, the alternate embodiment having lateral sides and grooves in the annular base confined to the portion of the annular base adjacent the lateral regions of the leaflets.
Figure 31:
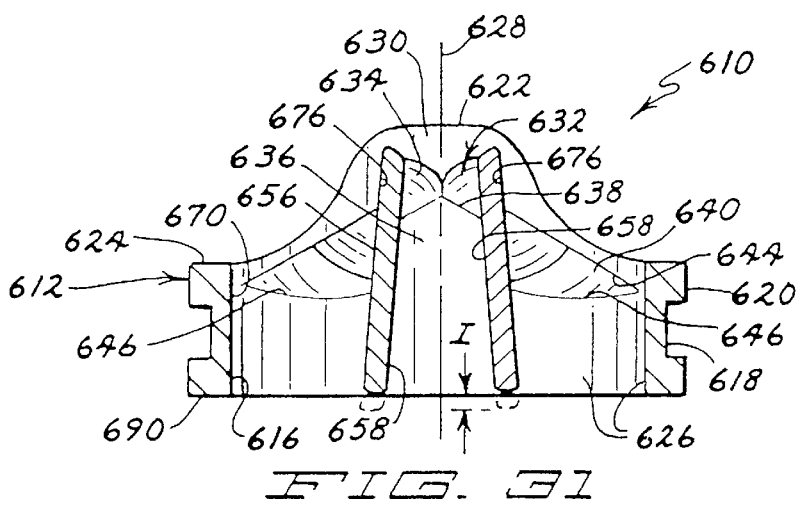
FIG. 31 is a cross-sectional view of the bileaflet heart valve of FIG. 30 showing the leaflets in the open position.
Figure 32:
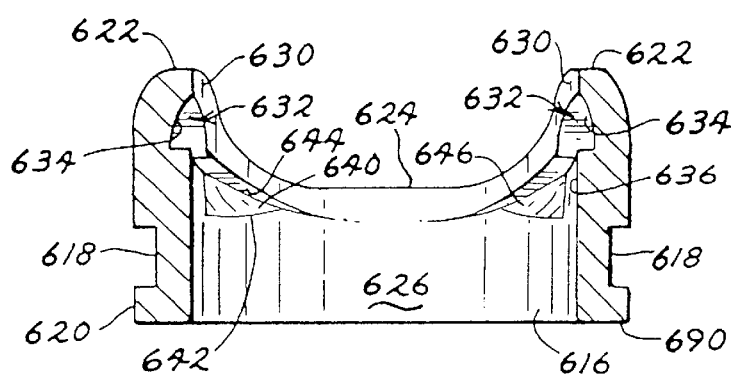
FIG. 32 is a transverse cross-sectional view of the annular base of the bileaflet heart valve of FIG. 30 with the leaflets omitted and showing one of the lateral sides of the annular base with a separation between the grooves defined by the inner wall of the annular base.

Referring now particularly to FIGS. 10, 13, 18–20, and 26–28, the relative degrees of translational movement between a leaflet 14' having a semi-circular pivot ear 84' (FIGS. 10, 18, and 25), a trapezoidal pivot ear 86 (FIGS. 19 and 26), and no pivot ear (FIGS. 13, 20, and 27) are diagrammed. Referring now especially to FIGS. 25–27, it will be appreciated that the translational movement $D_1$ for a semi-circular pivot ear 84 disposed between two flat edges 88' and within a semi-circular recess 32' will be limited by the spacing distance $X_1$ between the edge 88' of the pivot ear 84' and the wall of the recess 32', which is dependent upon the radii of both the pivot ear 84' and the recess 32'. Similarly, the translational movement $D_2$ for the trapezoidal pivot ear 486 is controlled by the height and baseline width of the pivot ear 486 and the depth and surface width of the recess 432, plus the relative angles of the beveling of the recess 432 and pivot ear 486. In practice, the translational movement $D_2$ of the trapezoidal pivot ear 486 is less than that ($D_1$) for a semicircular pivot ear 84', and may be selectively limited by increasing the width of the distal end of the pivot ear 84' relative to the recess 32', or decreasing the surface width of the recess 32' relative to the baseline width of the pivot ear 84'. Adjusting the bevel angles will also control the minimum spacing $X_2$ between the pivot ear 486 and recess 432.

By comparison, the translational movement $D_3$ of the lateral side region 262, 264 for an earless leaflet 214 of the present invention is limited only by the height of the leaflet 214 along the longest secant line S that can be draw bisecting the limited zone within the lateral side regions 262, 264 of the leaflet 214 between two points along the peripheral edge 250 which contacts the confronting curved radial surfaces of the recess 232. Consequently, the translational movement $D_3$ for an earless leaflet 214 can be increased significantly over that for a leaflet 14' or 414 having either a semicircular or trapezoidal pivot ear 84', 486 respectively. The degree of translational movement permitted for an earless leaflet 214 is therefore defined by the depth, width, and arc shape of the curved radial surfaces 282 of the recess 232 confronting the peripheral edge 250 of the leaflet 214 proximate the corresponding lateral side region 262, and the corresponding arc shape of the peripheral edge 250 of the leaflet 214.

Figure 20:
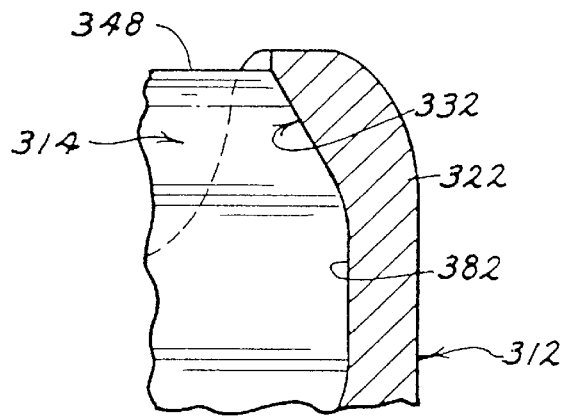
FIG. 20 is a lateral side elevation view of a recess and leaflet of the present invention with the leaflet in the fully upward (or open) translational position.
Figure 18:
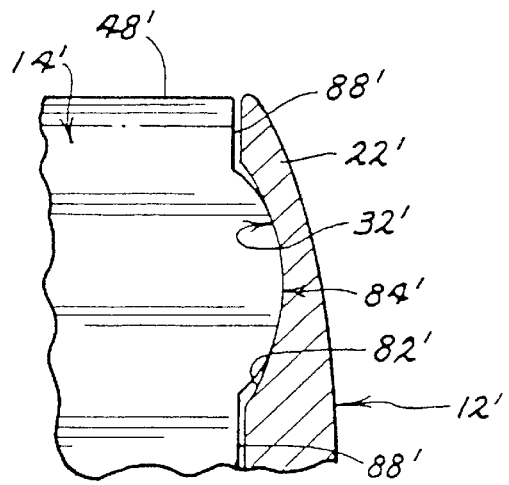
FIG. 18 is a lateral side cross sectional view of a recess of a prior art bileaflet heart valve, in which a leaflet is engaged which has a semi-circular pivot ear of the prior art similar to that shown in FIG. 10.
Figure 19:
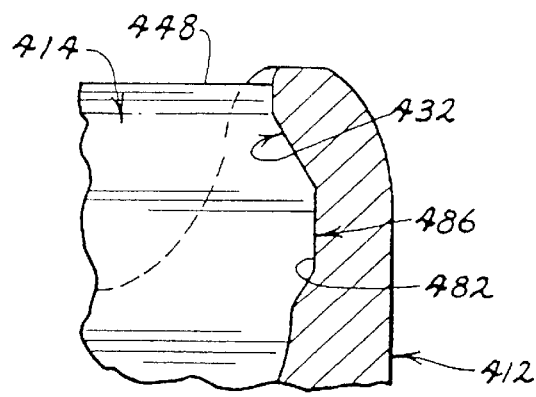
FIG. 19 is lateral side elevation view of a recess and leaflet having a trapezoidal pivot ear of the prior art.

Since the translational movement of the earless leaflet 214 can actually be controlled by adjusting the arc shape or curvature of the curved radial surfaces 282 of the recess 232 at either the top or bottom thereof, it is possible to define a recess 332 in which the profile of the peripheral edge 350 of the leaflet 314 mates substantially with the curved radial surfaces 382 of the recess 332 when the leaflet 314 is in the open position and disposed as high as possible on the annular base 312, as shown in FIG. 20. In such an instance, the degree of translational freedom for the leaflet is controlled by adjusting the arc shape at the bottom of the recess 332 relative to the shape of the peripheral edge 350 of the leaflet 314. This maximizes the translational movement available to the leaflet 314 when pivoting between the open position (where the leaflet 314 is in its lowest position relative to the annular base 312) and the closed position, prior to the leaflet 314 contacting the top of the recess 332 as shown in FIG. 20.

It will be appreciated that the peripheral edge 50 of the leaflet 14 may form composite curves within and between the lateral side regions 62, 64 and the central region 66, so that the separation or gap 72 between the side wall 26 or interior groove 40 is not affected by the curvature of the peripheral edge 50 within the lateral side regions 62, 64. Similarly, the maximum incursion or radial exposure is not adversely affected by the curvature of the peripheral edge 50 of the leaflet 14 within the lateral side regions 62, 64, except to the extent that downward translational movement of the leaflets 14 when the valve 10 is in the open position may be responsible for some incursion depending upon the height of the annular base 12, pivot axis, and shape of the leaflet 14.

Referring now to FIG. 4, it will be appreciated that despite the increased translational movement of the leaflets 14 compared with those having pivot ears 84 and 86, the peripheral edges 50 of the leaflets 14 exhibit little or no incursion below the bottom plane 90 of the annular base 12 even when the valve 10 is in the completely open position.

FIG. 4 depicts a substantially zero incursion distance I measured from the bottom plane 90 of the annular base 12 and the peripheral edges 50 of the leaflets 14. Even in a configuration where minimal incursion I is incurred, as depicted by the phantom lines in FIG. 4, it should be noted that radial exposure is confined to a region extending from a central plane (consistent with longitudinal axis 28) bisecting the lobes 22 of the valve 10 to a point approximately one-half the distance between the plane or longitudinal axis 28 and the side wall 26 of the bore 16. Similarly, that radial exposure is confined to approximately one-half or less of the distance between the plane or longitudinal axis 28 and the exterior surface 20 of the annular base 12. Lateral exposure is similarly negligible.

Referring now particularly to FIGS. 11–15, several embodiments of the earless leaflet are shown. For comparison, a conventional leaflet 14' having a semi-circular pivot ear 84' disposed between two flat surfaces 88' such as disclosed in the Hanson '658 patent is shown in FIG. 10.

FIG. 11 shows a leaflet 14 in which the peripheral edge 50 within the lateral side region 64 forms two composite curves 92, 94, the first curve 92 having a smaller radius r and being disposed more closely adjacent to the mating edge 48 than the second curve 94 having a greater radius R. The two curves 92, 94 meet at a junction 96 where the two curves 92, 94 are blended together smoothly. The primary distinction between this leaflet 14 and a conventional leaflet 14' having a pivot ear 84' as shown in FIG. 10, is that the first curve 92 is not bounded on both sides by a flat surface 88'.

Figure 17:
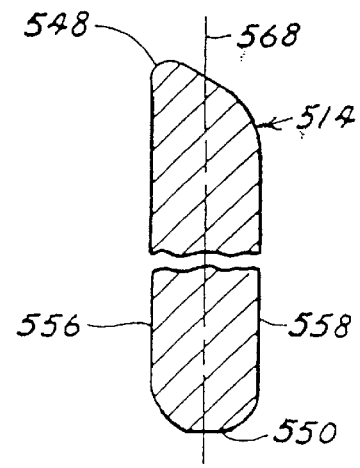
FIG. 17 is a cross-sectional view similar to that shown in FIG. 16, but of an alternate embodiment of a leaflet similar to that shown in FIG. 11.

As shown in FIG. 16, the mating edge 48 is angled from the top planar surface 56 to the bottom planar surface 58 at an angle of about 40° to about 60° relative to the planar axis 68 of the leaflet 14. Referring now also to FIG. 17, it will be appreciated that the exposed edges 48, 50 of the leaflet 14 extending between the planar surfaces 56, 58 may be rounded, radiused, or beveled as desired in a manner similar to that shown in FIG. 17. Because the surfaces within the pivotal region sweep a plane and a spherical section when the leaflet 14 pivots, the configuration shown in FIG. 11 is termed a flat spherical (FS) design. It will be further appreciated that while the peripheral edge 50 in the central region 66 can be completely curved along the radius of the second curve 94, the overall height of the leaflet 14 described above represents the truncation of the central region by a flat portion 98, thereby presenting a gap or separation 72 to mitigate against cavitation as described above.

FIG. 12 illustrates a variation of the leaflet 14 shown in FIG. 11, wherein the first curve 92" is connected to the first endpoint 52" by a line intersecting the first endpoint 52" and laying tangential to the first curve 92". The dimensions of this leaflet 14" are generally the same as the dimensions of the leaflet 14 of FIG. 11, with the exception that the length of the mating edge 48". Because the surface within the pivotal region sweep out a conical and a spherical section when the leaflet 14" pivots, this configuration is termed a cone spherical (CS) design.

Figure 13:
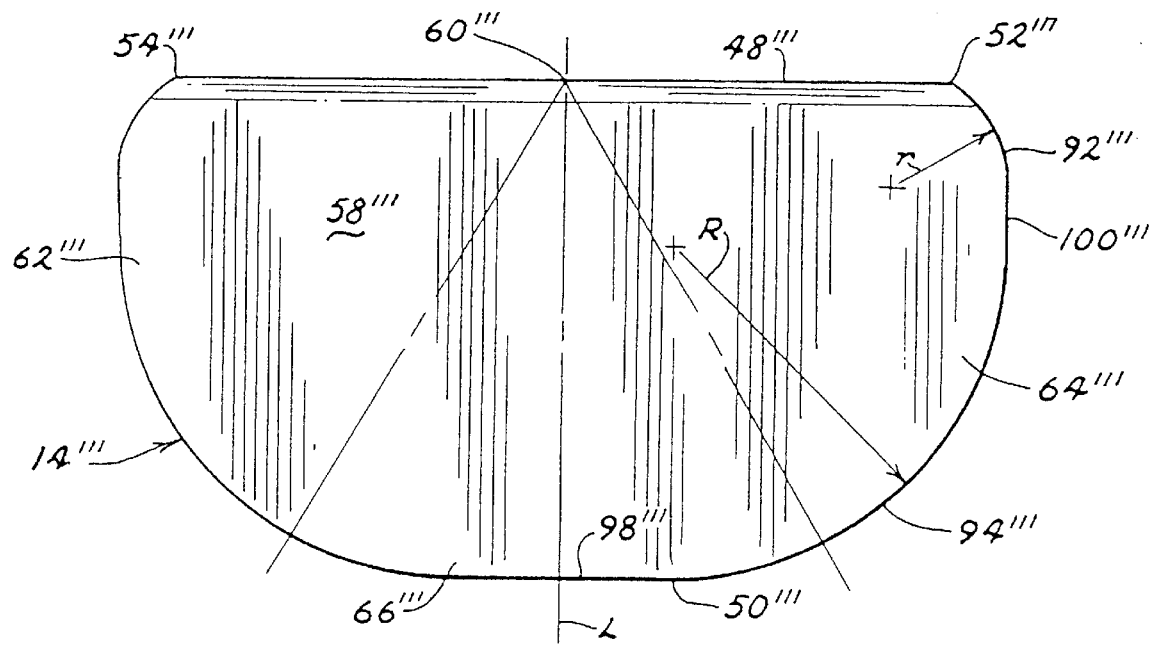
FIG. 13 is a bottom plan view of a second alternate embodiment of the leaflet shown in FIG. 11.

FIG. 13 illustrates a further embodiment termed a spherical flat (SF) design, in which the first curve 92'" and second curve 94'" are divided by a flat region 100'".

FIG. 14 illustrates a similar embodiment termed a conical flat (CF) design, in which a first flat segment 102"" extends from the first endpoint 52"" of the mating edge 48"" to a point tangential with the first curve 92"", which is a small radius r into a second flat segment 104"", and which progresses to a second curve 94"".

FIG. 15 illustrates a more complex embodiment termed a cone spherical cone (CSC) design that is similar to that of FIG. 14 with the exception that the second flat segment 104'"" is not parallel with the centerline L bisecting the mating edge 48'"" at the center point 60'"". In this embodiment, the peripheral edge 50'"" extends from the first endpoint 52'"" of the mating edge 48'"" along a first flat segment 102'"" a first curve 92'"" having a radius r which progresses to a second curve 94'"" having a radius R. Alternately, the first flat segment may also be a composite of two differently angled straight sections (not shown) with the section most closely adjacent the mating edge flaring or tapering outwardly relative to the next adjacent flat section, thereby creating two conical zones adjacent to the mating edge.

Figure 21:
FIG. 21 is a perspective view of a monoleaflet heart valve with anterior orientation as known to the prior art.
Figure 22:
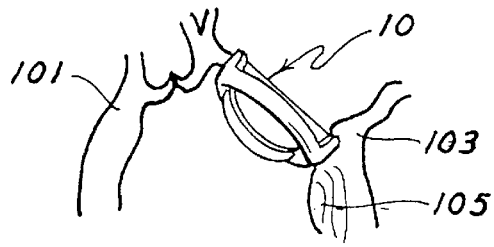
FIG. 22 is a perspective view of a bileaflet heart valve with anti-anatomical orientation.
Figure 23:
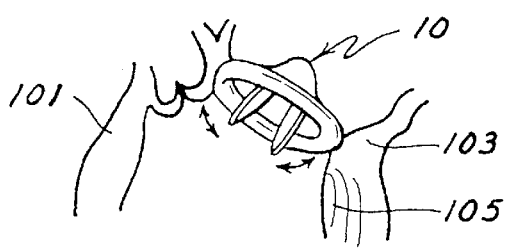
FIG. 23 is a perspective view of a bileaflet heart valve with anatomical orientation.
Figure 24:
FIG. 24 is a perspective view of a monoleaflet heart valve with posterior orientation as known to the prior art.

Referring again to FIGS. 21–24 and FIG. 29, a bileaflet heart valve 10 of the present invention is shown diagrammatically implanted within the heart 101 of a patient, with the valve 10 sutured in place proximate to the mitral annulus 103 of the anatomical coronary valve and disposed above the papillary muscle and tendineae chordae 105 fixed to the posterior mitral annulus as described previously. The bileaflet valve 10 may be implanted in either the fully anatomical orientation or the fully anti-anatomical orientation as shown in FIGS. 22 and 23, respectively, or adjusted between the fully anatomical and anti-anatomical orientations by rotating the valve 10 within the corresponding suture ring (not shown) as is well known to the art. These orientations may be compared with the anterior and posterior orientations of a monoleaflet valve M shown in FIGS. 21 and 24.

Referring now particularly to FIGS. 30–34 and 37–38, alternate embodiments of the bileaflet heart valve 610, 610' and 710 of the present invention are shown. These embodiments have been generally described above with reference to yet other embodiments, and are described separately herein in greater detail with the understanding that these alternate embodiments may be combined with other features and elements of the bileaflet heart valve 10 in yet other embodiments.

It will be appreciated that the inner wall 626 of the annular base 612 may be fabricated such that a smooth and continuous surface forms a separation between opposing sides of the groove 640, with the top edge 644 of the groove 640 contacting the leaflets 614 only within the lateral regions 662, 664 defined by lines oriented at an angle of approximately 60° relative to the centerline L of the corresponding leaflets 614.

Figure 33:
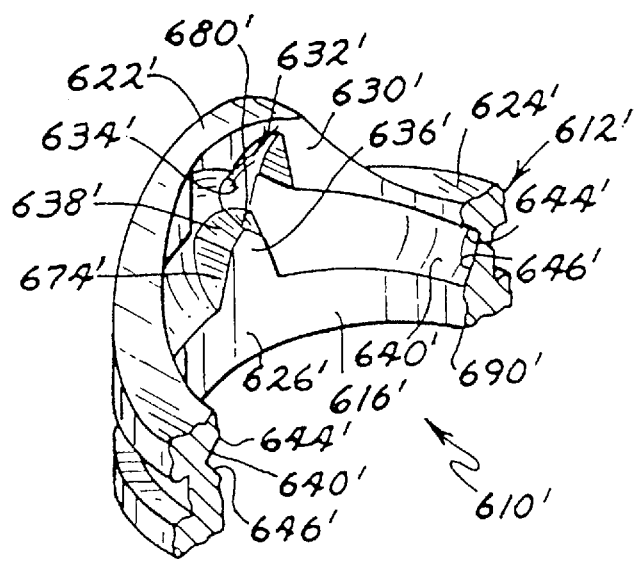
FIG. 33 is a partially broken away lateral perspective view of the an alternate embodiment of the bileaflet heart valve prosthesis of FIG. 1 showing the top surface of the separator body and the side surfaces of the recesses beveled away from a line perpendicular to the longitudinal axis.
Figure 34:
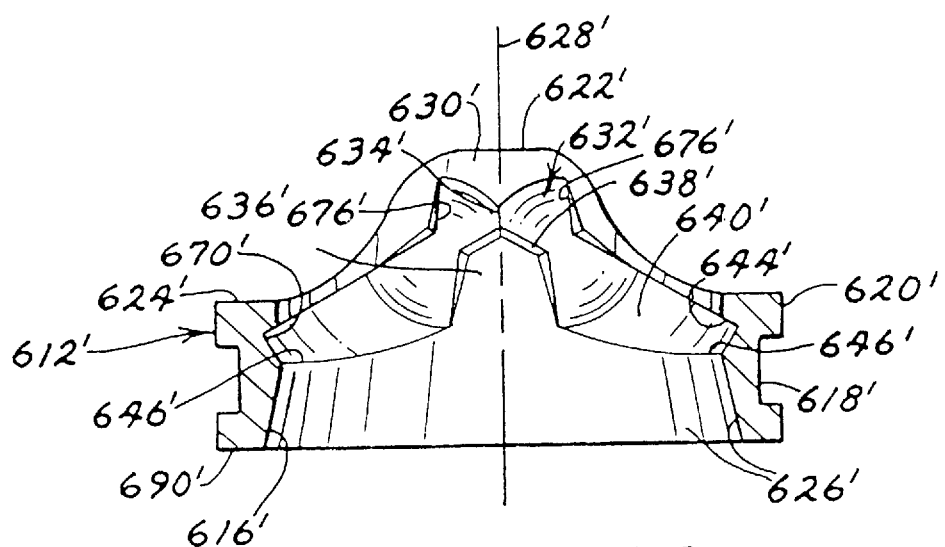
FIG. 34 is a cross-sectional view similar to that shown in FIG. 3 of the annular base of the bileaflet heart valve prosthesis of FIG. 33 showing the orientation of the beveled surfaces.

Referring now specifically to FIGS. 33 and 34, the top surfaces 638' and side surfaces 674' of the separator body 636', the side surfaces 676' of the recesses 632', and the top edge 644' of the groove 640' adjacent the recesses 632' are each beveled or tapered away from a normal orientation as previously shown in FIGS. 3, 4, 8, and 9 in which the surfaces 38, 74, 76, 44 and corresponding junction edges are oriented in planes which are generally parallel with radial lines (not shown) extending away from the annular base 12 in a direction perpendicular to, and intersecting with, the longitudinal axis 28. As such, in the beveled or tapered embodiment shown in FIGS. 33 and 34, corresponding surfaces 638',674',676',644' are oriented at an acute angle relative to those radial lines extending away from the annular base 612' in a direction perpendicular to and intersecting with the longitudinal axis 628', thus forming generally pyramidal or trapezoidal structures when viewed from the perspective of the longitudinal axis 628' as shown in FIG. 34.

Figure 37:
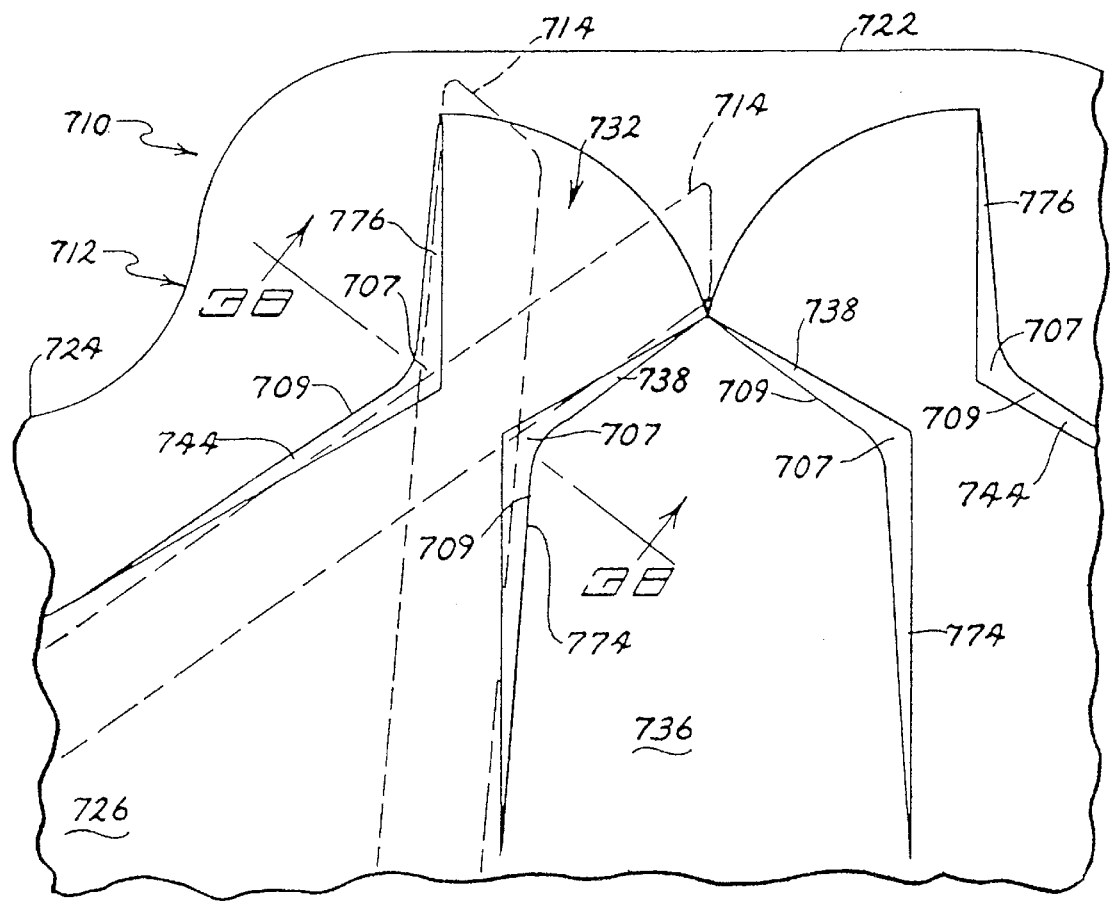
FIG. 37 is a diagrammatic view of the recess in the annular base receiving a leaflet shown in phantom pivoting between the open and closed positions, showing the beveled arcuate surfaces along which the edges of the leaflet roll as the leaflet pivots between the open and closed positions.
Figure 38:
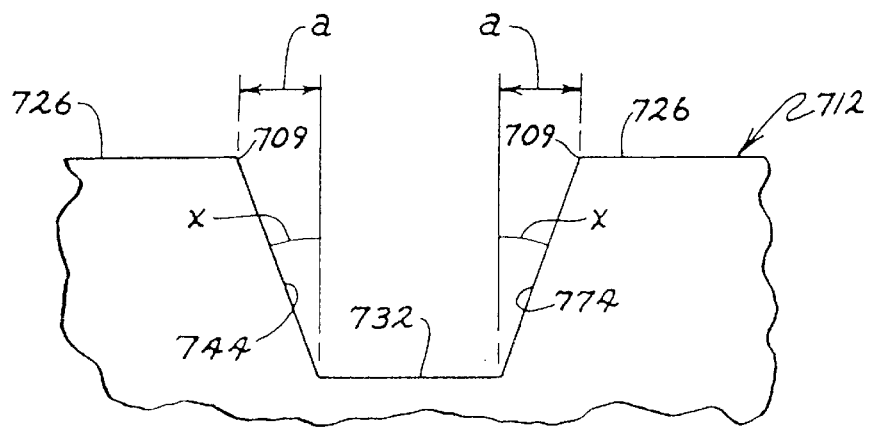
FIG. 38 is a side elevation view taken from line 38—38 in FIG. 37 showing the beveled surfaces extending between the lateral wall and the bore and the floor of the recess, and the floor of the recess and the face of the separator body.

Referring now particularly to FIGS. 37 and 38, the beveled or tapered surfaces 744, 776 between the inner or lateral side wall 726 of the bore 716 and the floor of the recess 732, and the beveled or tapered surfaces 738, 774 between the lateral side wall 732 of the separator body 736 and the floor of the recess 732, are shown diagrammatically in greater detail. Referring to FIG. 37, it will be appreciated that the two pairs of beveled surfaces 744, 776, and 738, 774, respectively, are joined along a radius to form a generally smooth and continuously arcuate path 707 along which the corresponding regions of the peripheral edge 750 of the appropriate leaflet 714 will pivot or "roll" as the leaflet 714 pivots or moves between the open and closed positions, thereby distributing stress and frictional forces over an extended area of the peripheral edge 750 of the leaflet 714 and the generally smooth and continuously arcuate path 707. Referring to FIG. 38, a bevel angle "x" will range from 20° to 40°, with a preferred angle "x" of approximately 30°, measured relative to perpendicular with either the lateral side wall 26 of the bore 16 or the floor of the recess 32, will result in the junctions 709 between the lateral side wall 726 along the bore 716 or the face of the separator body 736, and the beveled surfaces 744, 776 and 738, 774 respectively, being spaced apart from the normal or perpendicular lines intersecting the beveled surfaces 744, 776, and 738, 774 and the floor of the recess 732 by a distance "a" on the order of 0.008"–0.020" measured along a line parallel with the longitudinal axis 728.

Figure 35:
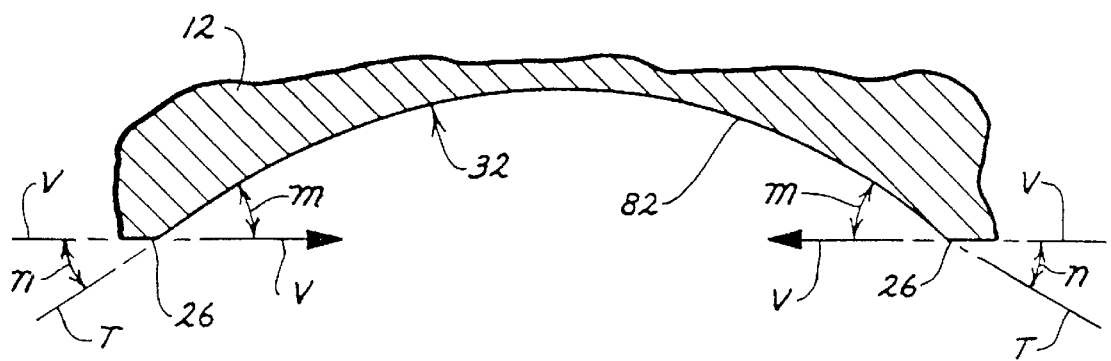
FIG. 35 is a diagrammatic view of a recess in the bore of the bileaflet heart valve of FIG. 1 showing the angle formed between the lateral wall of the bore and the tangential adjoining surface of the recess.

Referring now particularly to FIG. 35, a recess 32 in the side or lateral wall 26 of the bore 16 is shown diagrammatically, the recess 32 forming an angle "n" of 35° or less between the lateral wall 26 and a line "T" tangential with the surface of the recess 32 closely proximate to and adjoining or intersecting the lateral wall 26. It will be appreciated that the intersection between the lateral wall 26 and recess 32 may be radiused, angled, or tapered slightly, either intentionally or due to the limitations of fabrication, however such radiusing, angling, or tapering is disregarded in measuring the angle between the lateral wall 26 and the line "T" tangential in the region closely proximate to the lateral wall 26. This angle will be the same as the angle formed between the optimal laminar flow vector "V" of the blood circulating in either the antegrade and retrograde directions closely adjacent to and parallel with the lateral wall 26 within the bore 16 of the valve 10 in the regions approaching the recess 32, with a portion of the blood diverting from this optimal laminar flow vector "V" to traverse along the surface of the recess 32. An angle "m" of approximately 30° has proven to be effective to achieve the desired effect in providing a cleansing blood flow within the recess 32 proximate to the intersection between the lateral wall 26 and surface 82 of the recess 32. However, it will be appreciated that angles of varying degree measuring less than 35° may similarly be suitable or even more effective in other applications or embodiments.

Figure 36:
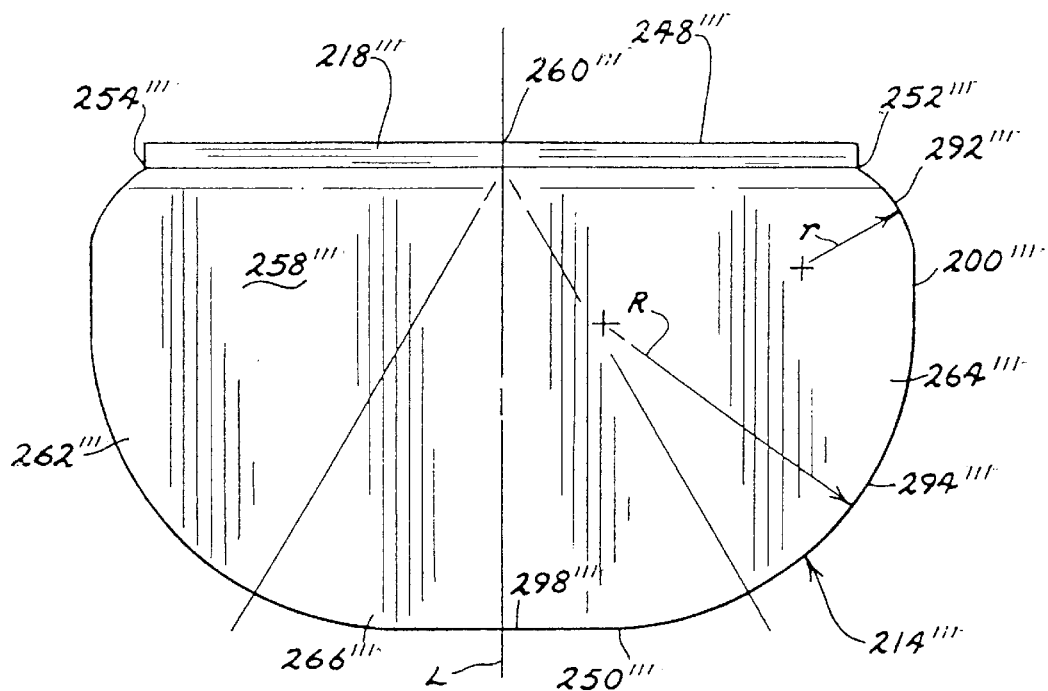
FIG. 36 is a bottom plan view of an alternate embodiment of a leaflet for use with the bileaflet heart valve prosthesis of this invention, that embodiment being similar to the embodiment of FIG. 13 and including a generally rectangular extension or lip along the mating edge.
Figure 39:
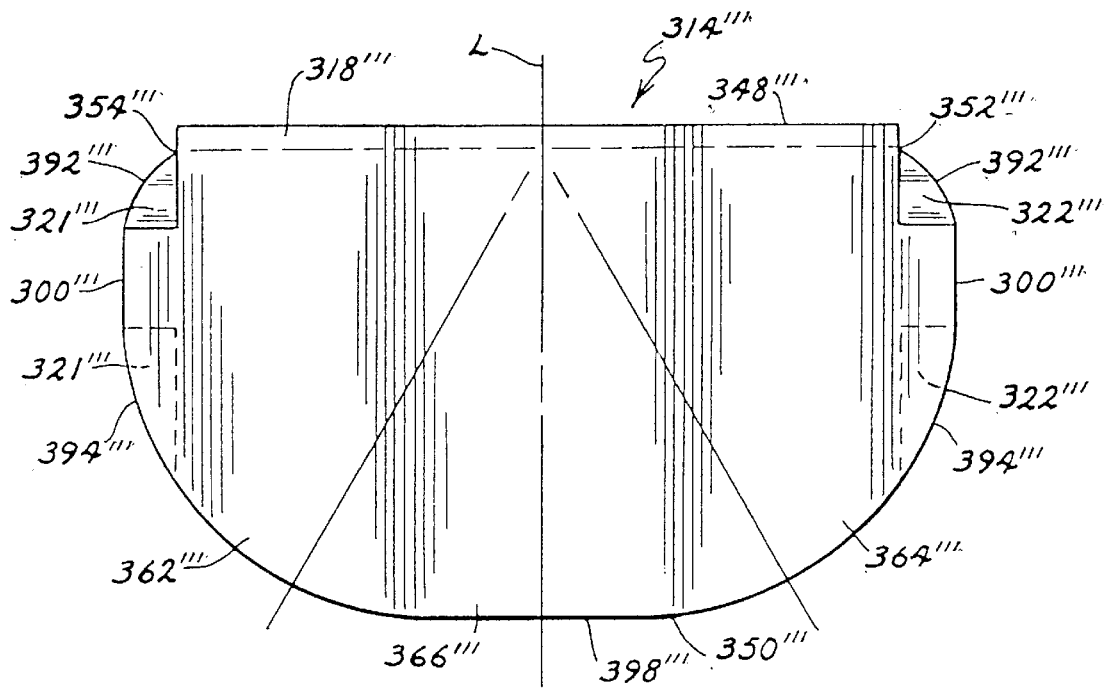
FIG. 39 is a top plan view of an alternate embodiment of a leaflet for use with a bileaflet heart valve of the present invention, that embodiment having portions adjoining the flat side surfaces removed along an opposingly angled path to form two sets of beveled notches in the opposing side edges of the leaflet.
Figure 40:
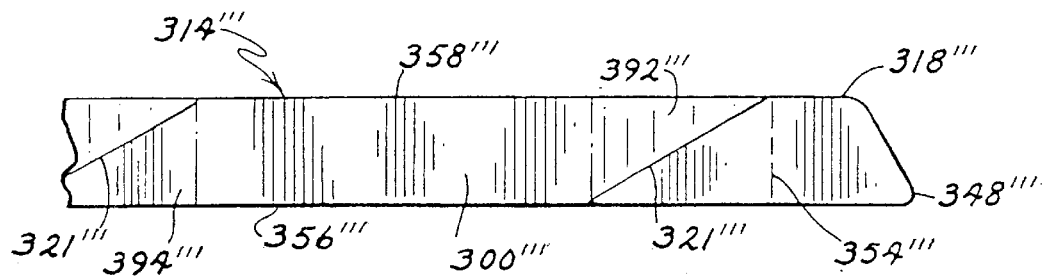
FIG. 40 is a side evaluation view of the leaflet of FIG. 39, with the leaflet inverted, showing a single set of two notches disposed on opposing sides of the leaflet.
Figure 41:
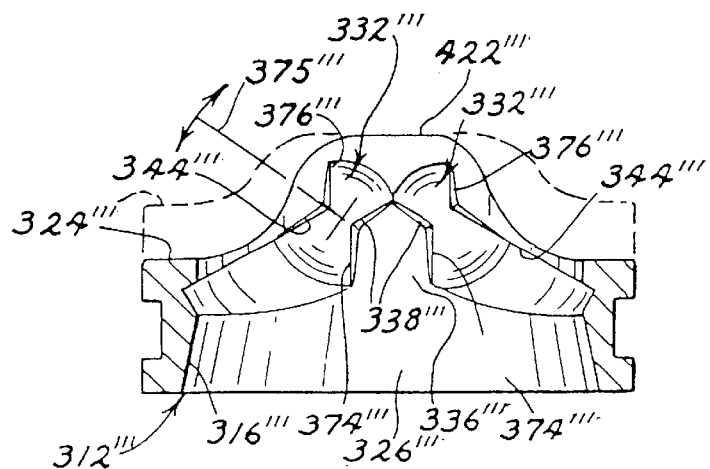
FIG. 41 is a diagrammatic side elevation view of the annular base of a bileaflet heart valve of the present invention, showing a raised lateral wall and reduced lobe height compared with the annular base of FIG. 3.
Figure 42:
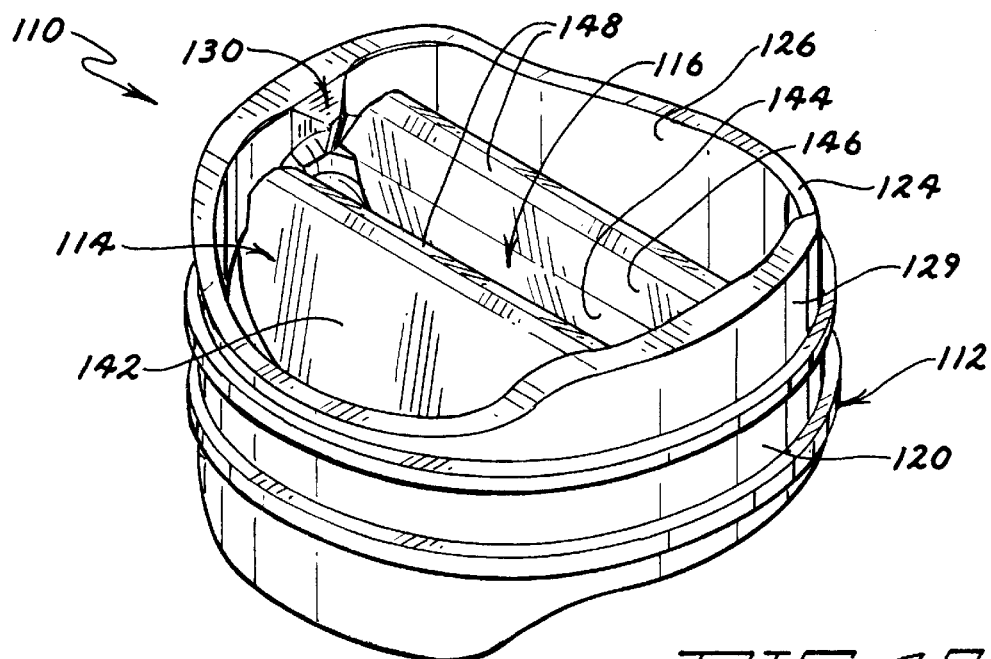
FIG. 42 is a perspective view of a preferred embodiment of the present invention showing the leaflets in a fully open position.
Figure 43:
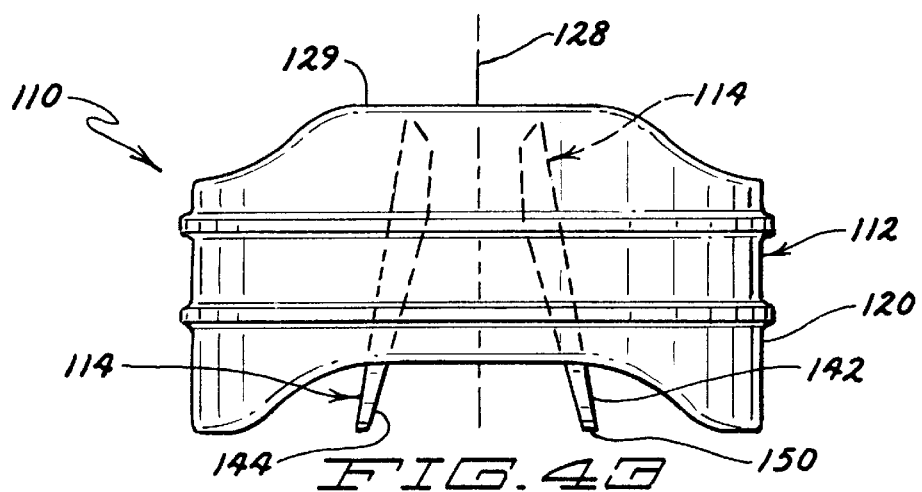
FIG. 43 is a lateral side view of the preferred bileaflet heart valve of the present invention shown in FIG. 42.
Figure 44:
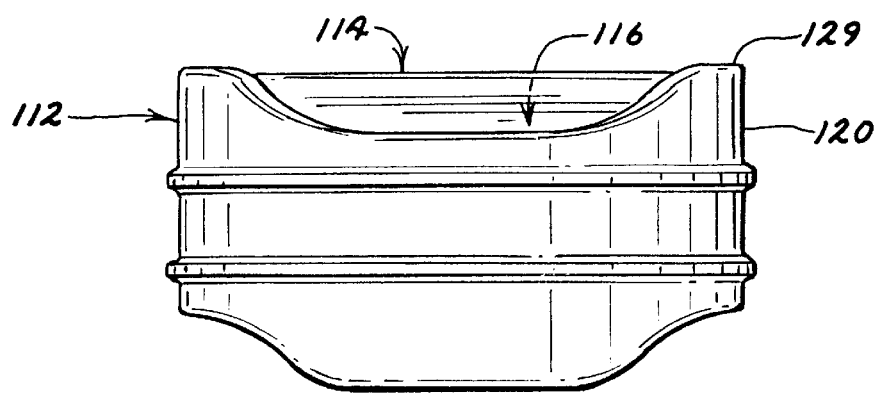
FIG. 44 is a lateral side view of the preferred bileaflet heart valve shown in FIG. 42.
Figure 45:
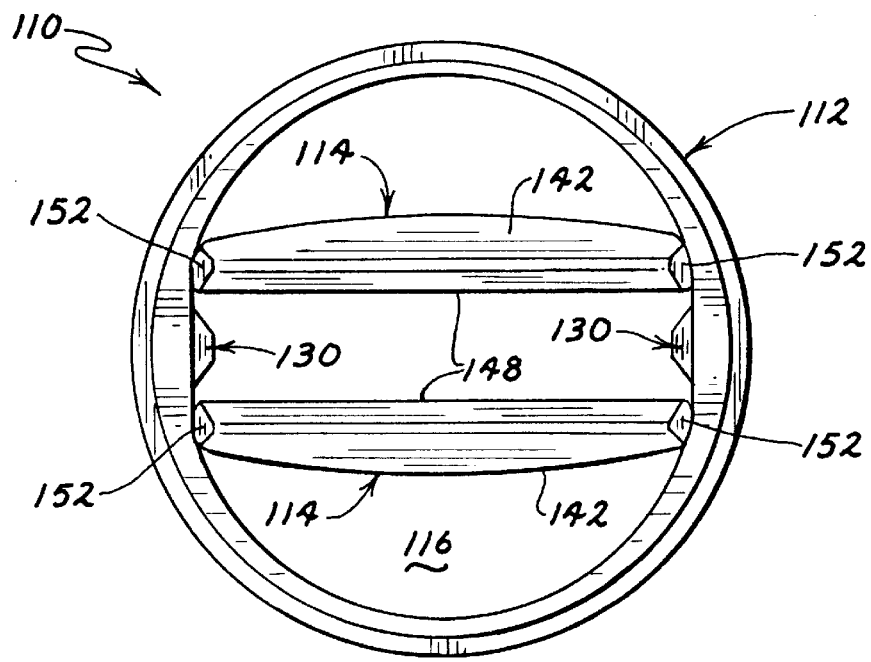
FIG. 45 is a top plan view of the preferred bileaflet heart valve shown in FIG. 42.
Figure 46:
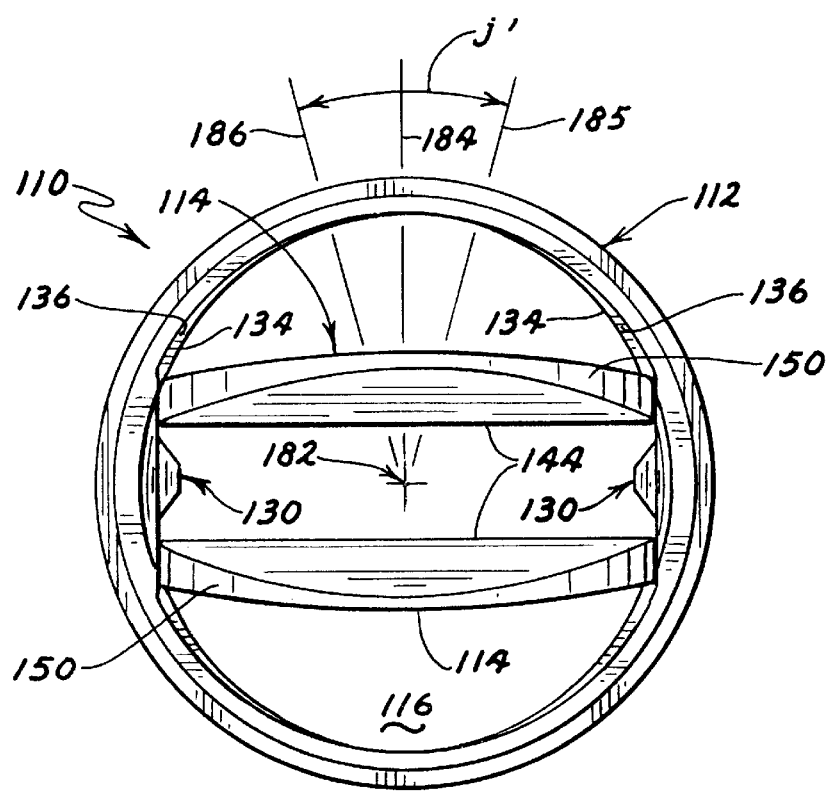
FIG. 46 is a bottom plan view of the preferred bileaflet heart valve shown in FIG. 42.

Referring now to FIGS. 36 and 39–40, alternate embodiments of the leaflet 14 shown in FIG. 13 are described. The elements of the leaflet 214''' of FIG. 36 conform substantially to those of the SF design shown in FIG. 13, with the addition of a generally rectangular flange or lip 218''' disposed along and extending from the mating edge 248''' of the leaflet 214''', thereby resulting in a displaced mating edge 248'''.

The elements of the "twist" embodiment of the leaflet 314''' shown in FIGS. 39 and 40 conform substantially to those of designs shown in FIGS. 11, 13 and 36, but further define two pairs of beveled notches 321''', 322''' formed by removing portions of the side edges 392''', 394''' of the leaflet 314''' adjacent to and bounded by the two curved segments 392''', 394''' along angled paths extending between the two planar surfaces 356''', 358''' he leaflet 314'''. It will be appreciated that the notches 321''', 322''' are formed in one or both planar faces 356''', 358''' of the leaflet 314''' adjacent one or both side edges 392''', 394''', 300''' of the leaflet 314''', and may extend at any angle up to the angle defined by the angled paths extending completely between the planar faces 356''', 358''' incorporating such angled notches 321''', 322''' into regions of the leaflet 314' adjacent the two curved segments 392''', 394''' of the peripheral edge 350''', and permitting the lateral stability of the leaflet 314''' within the annular base 312''' to be maintained by the intervening flat side edges 300''' and the flange or lip 318''', the angles of the contact surfaces 374''', 376''' defined by the recesses 332''' into the lateral wall 326''' of the annular base 312''' and the separator body 336''' will be reduced an amount generally proportional to the particular angle formed between the angled surfaces of the notches 321''', 322''' and the planar faces 356''', 358''' of the leaflet 314'''.

Providing two sets of diagonally opposing notches 321''', 322''' on each planar face 356''', 358''' of each leaflet 314''' corresponding to the regions of contact between the surfaces 374''', 376''' of the recess 332''' which prevent pivotal movement of the leaflet 314''' beyond the open position will permit the "top" of surface 376''' and the "bottom" of surface 374''' to be moved angularly inward and the "bottom" of surfaces 374''' to be moved angularly outward relative to the corresponding positions of those surfaces 374''', 376''' if the leaflet 314''' did not possess the notches 321''', 322''' to define a narrower recess 332'''. Since the increased angle of the surfaces 374''', 376''' relative to the longitudinal axis 328''' means that the cutting tool (not shown) used to remove portions of the lateral wall 326''' of the annular base 312''' to form the recesses 332''' need only pivot through a narrower or lesser arc, the height of the top surface 324''' of the annular base 312''' may be increased correspondingly as shown in a phantom in FIG. 41 and still permit clearance as the cutting tool (not shown) pivots through the arc necessary to define the contact surfaces 374''', 376''' of the recesses 332'''. Raising the height of the top surface 324''' of the annular base 312''' has the effect of increasing the length and uniformity of the bore 316''', and effectively lowering the relative height of the lobes 422''', resulting in the advantages previously discussed. Similar results could be achieved regarding the contact surfaces 338''', 344''' defining the closed position of the leaflets 314''', however, the generally open top of the annular base 312''' and bore 316''' mitigate against interference with the cutting tool (not shown) when pivoted to define those surfaces 338''', 346''', and this process would result in reducing the available angle of the notches 321''', 322''' aligned with the contact surfaces 374''', 376''' corresponding to the open position due to the presence of the aligned notches 321''', 322''' on the opposing planar surfaces 356''', 358''' of the leaflet 314'''.

Bileaflet heart valve prostheses 10, 110 of the present invention are preferably fabricated from a metal such as titanium, a carbon compound (or carbon with a minor percentage of silicon) such as pyrolytic carbon or the like, a metal alloy, or a suitable substrate coated with pyrolytic carbon as are well known in the art.

Referring now to FIGS. 42–67, preferred embodiments of the bileaflet heart valve prosthesis 110 are described. The preferred embodiment of the bileaflet heart valve 110 of the present invention shown in FIG. 42 includes an annular base 112 and first and second leaflets 114. The first and second leaflets 114 are mounted within the annular base 112 for pivotal movement between a fully open position, shown in FIGS. 42–46 and diagrammatically in FIG. 56, and in phantom in FIG. 57, and a fully closed position shown in FIGS. 64–65 and diagrammatically in FIG. 57. The annular base 112 has a top surface 124 and an inner wall 126 which defines a generally circular bore 116 passing through the annular base 112 in a direction generally parallel with a longitudinal axis 128 oriented generally in parallel with a path for circulation of fluid or blood through the bore 116.

The top surface 124 of the annular base 112 is raised proximate opposing lateral sides 129. On the inner wall 126 of the annular base 112 proximate the opposing lateral sides 129, flow diverter protrusions 130 extend away from the inner wall 126 toward a center 182 of the annular base 112 and the circular bore 116. The flow diverter protrusions 130 are placed generally between a pair of recesses 132 in each of the respective lateral sides 129 of the base 112.

Referring now to FIGS. 42–49 and 58–59, the recesses 132 extend into the respective lateral sides 129, thereby displacing a cylindrical bottom surface 140 of the recess 132 from the respective lateral surface 133 proximate the respective lateral side 129 and the respective recess 132. In preferred embodiments of the present invention, the recesses 132 extend away from the flow diverter protrusions 130. As the recess 132 extends away from the flow diverter protrusion 130, it passes through a cylindrical radius which is "feathered out" as the cylindrical surface 140 approaches a junction with the respective lateral surface 133.

Figure 59:
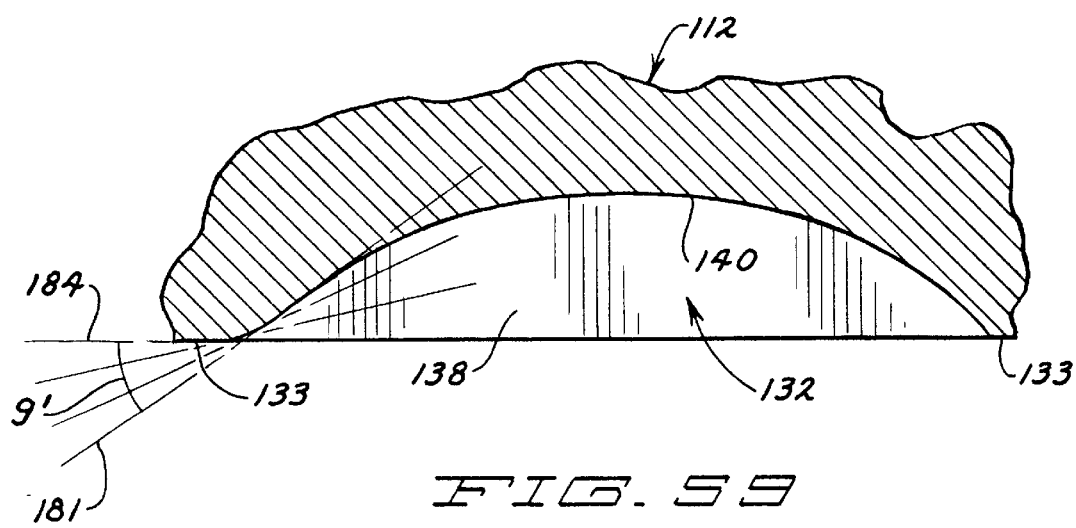
FIG. 59 is a partially broken away cross-sectional view of the recess as seen from the line 59—59 of FIG. 48.

As shown specifically in FIG. 59, a line 181 which is tangential with a point on the cylindrical bottom surface 140 of the recess 132 just prior to a further point at which the cylindrical surface 140 is "feathered out" to form a junction with the lateral surface 133 lies at an angle "g'''" to a tangent line 184 which intersects line 181 and is tangential to the lateral surface 133. In order to properly measure the entrance angle, "g'''", to the recess 132 a number of lines similar to line 181 which are tangential to a point on the cylindrical surface 140 must be considered. This may be an infinite number of lines. The entrance angle, "g'''", will be the angle between the lines 184 and 181 which will be the greatest angle that exists between the line 184 and any of the lines which can be drawn which intersect with line 184 and are tangential to a point on the cylindrical surface 140. This angle "g'''", is representative of a recess entrance angle to the cylindrical recess 132. In preferred embodiments the recess entrance angle is less than about 35°. Preferably, the recess entrance angle "g'''" is between about 15° and about 35°. More preferably, the recess entrance angle "g'''" is from about 18° to about 34°. In even more preferred embodiments, the recess entrance angle "g'''" ranges from about 21° to about 33°. It will be appreciated that recesses to retain pivotal leaflets have existed in the bileaflet heart valve prostheses of the prior art for some time. It is believed that a lower recess entrance angle will facilitate washing of the recess to minimize stagnation and potential for thrombogenic events in proximity to the recess 132. Therefore, it is believed that diminishing the angle of entrance to the recess 132 will provide for better washing activity and lessen any potential for embolism which may exist in patients utilizing prosthetic heart valves.

The flow diverter protrusion 130 also helps to divert blood passing through the circular bore 116 into the recesses 132. It will be appreciated that the protrusion 130 can channel fluids passing through the bore 116. Since the protrusion 130 lies at one end of the respective recesses 132, as is clearly illustrated in FIG. 48, a portion of the blood flowing into the circular bore 116 when the leaflets 114 are in an open position will channel around the flow diverter protrusion 130 and into the adjacent recesses 132 and along the bottom side wall 138 of the cylindrical recess 132. In preferred embodiments of the present bileaflet heart valve prosthesis 110 of the present invention, the side wall 138 may be beveled in a manner demonstrated in phantom in FIG. 58 to form a side wall 138'.

As shown particularly in FIGS. 50–55, the leaflets 114 have a top planar surface 142 and a beveled bottom surface having a peripheral bevel 144 proximate the peripheral edge 150 and a central bevel 146 proximate a mating edge 148 which is preferably a straight edge having a flat surface. When the respective leaflets 114 pivot to reside in the fully closed position, the mating edges 148 of the respective leaflets mate together to significantly obstruct blood flow through the very limited space between the respective mating surfaces 148. Lateral sides 151 of the respective leaflets 114 have a cylindrical surface proximate the diamond surface 154. Generally V-shaped notches 153, 155 are located adjacent to the diamond surface 154. The inflow notches 153 are located generally between the diamond surface 154 and the angular flat surface 152. The generally V-shaped notch 153 is created by an inflow flat 160 and an inflow side wall 156 of the cylindrical diamond surface 154. The generally V-shaped notch 155, namely the outflow notch 155, is defined by an outflow flat 162 and an outflow side wall 158 of the diamond surface 154. As shown particularly in FIGS. 52 and 53, a beveled outflow side wall "158'''" may be provided as shown in phantom in those Figures. The beveling of the outflow side wall "158'''" also extends around to a portion of the side surface "161'''" proximate the diamond surface 154 which would be part of the central bevel surface 146 or the portion of the surface 161 if not beveled. This beveling is designed to cooperate with the beveling of the side wall 138 to form the beveled side wall "138'" shown in FIG. 48 and 58. The beveled portions of the respective surfaces "158'", "161 '" and "138'" will cooperate to retain the leaflets 114 within the recess 132 and permit greater cleansing of recesses 132 and greater "sweeping" of the surfaces in these areas.

Figure 64:
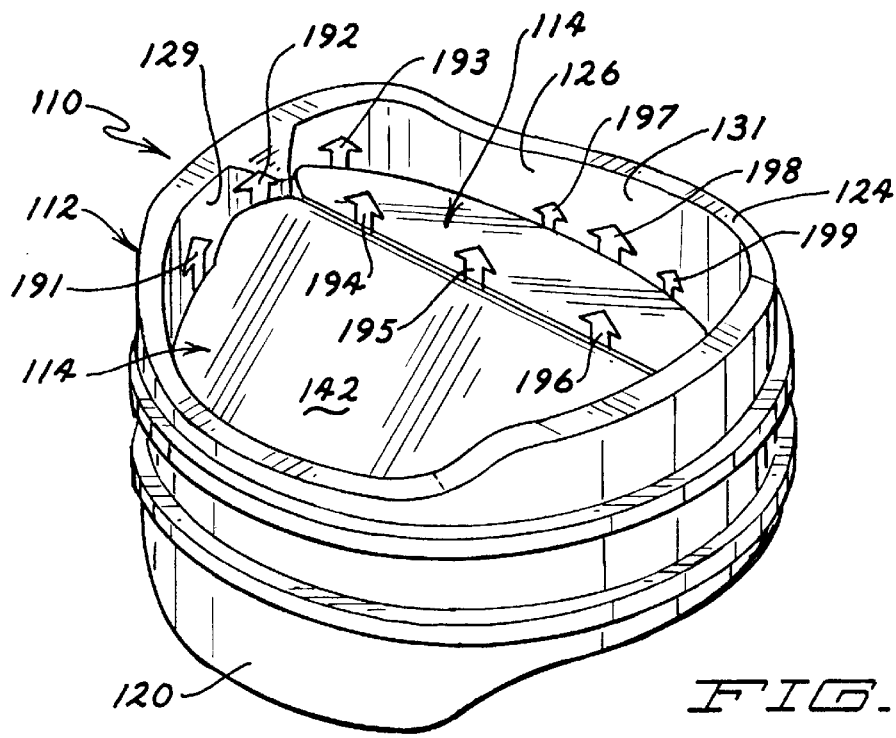
FIG. 64 is an elevated perspective view of the preferred bileaflet heart valve of the present invention similar to that shown in FIG. 42, except that the leaflets are in a fully closed position.

As previously discussed herein, washing of the various surfaces, crevices and the like by blood fluid passing through the heart valve prosthesis 110 is believed to be particularly important to reduce stagnation and potentially thrombogenic activity. The present bileaflet heart valve 110 is designed with this in mind. All of the surfaces of the present valve 110 are actively washed at one time or another in the pumping cycle of the heart in which the valve 110 is implanted. When the valve 110 is in the fully opened position all of the surfaces of the side wall 126 are actively washed and the flow diverter protrusion 130 is actively washed as it channels blood into the recesses 132 and particularly toward the side wall 138 or its beveled counterpart "138'". The leaflets 114 are also actively washed as the blood flows in the antegrade direction through the bore 116. In addition, the flow diverted protrusion 130 channels blood into the recess 132 proximate the diamond surface 154 on the lateral side of the leaflet 114 which can rest against the cylindrical bottom surface 140 of the recess 132. The diamond-shaped cylindrical surface 154 also has a cylindrical radius generally consistent with the cylindrical radius of the bottom surface 140 of the recess 132. Each leaflet 114 also has an angular surface 152 which directs a certain amount of blood flowing in an antegrade direction, when the leaflets 114 are in an open position, to the inflow side wall 156 of the diamond surface 154. As shown particularly in FIG. 64, when the leaflets 114 are in a fully closed position, some regurgitation of blood through the bileaflet valve 110 occurs in the retrograde direction. The regurgitation is desirable to a certain degree, so long as the energy efficiency of the pumping activity of the heart is not compromised. The regurgitation occurs in a number of areas. Referring now also to FIG. 64, and the other illustrations of the preferred bileaflet heart valve 110, retrograde blood flow may pass between the mating surfaces 148 of the respective leaflets 114 as demonstrated by arrows 194, 195 and 196 in FIG. 64. The bottom of the flow diverter protrusion 130 also channels retrograde blood flow into the recesses 132 where it will be directed up against the seats 136 created by the separation between the cylindrical bottom surface 140 and the upper edge 134 of the recess 132. An outflow side wall 158 of the diamond surface 154 may also channel retrograde blood flow to the recess 132 and particularly to the seat 136. This flow will then regurgitate between the leaflet 114 and the side wall 126 after it flows over the seat 136 and come out proximate the regurgitation representation arrow 191 in FIG. 64. Additional retrograde blood flow will simply wash the flow diverter protrusion 130 and channel upwards proximate arrow 192 in FIG. 64. It will be appreciated that there will almost always be at least some separation between the peripheral edge 150 of the leaflet 114 and the side wall 126. This enables retrograde blood flow to regurgitate between the peripheral edge 150 and the side wall 126 proximate the entire peripheral edge 150. The regurgitation is particularly significant proximate the transverse sides 131. This is particularly true because of the side wall surface 126 proximate the center of the peripheral edge 150 is flush, thereby providing no obstruction to the retrograde flow of blood. It will be appreciated that the seat 136 is fully diminished to nothing in this area in preferred embodiments. A further discussion of the seats 136 follows a further description of the leaflets 114 immediately below.

Referring now particularly to FIGS. 56–57 and 60–61, a certain amount of "play" exists between the respective surfaces in the area of the diamond surface 154 and the recess 132 when the leaflets 114 are in the open position. This "play" permits a significant amount of translational movement. Because of the increased potential for translational movement between these surfaces when in the open position, the leaflets 114 have greater freedom for translational motion than is either exhibited or generally possible in any of the prior art valves which have "matched" or "parallel" surfaces in both the open and closed positions. This potential for translational movement is not present when the leaflets 114 are in the closed position.

An axis 165, parallel with respective cylindrical surfaces on "diamond" surfaces 154 of the respective leaflets 114, and perpendicular the top surface 142 will lie at an angle "k" to an axis 167, parallel with the respective cylindrical bottom surface 140 of respective recess 132, and perpendicular with the upper edge 134 of the recess 132, when the leaflets 114 are in the fully opened position. When the leaflets 114 are in the fully closed position these respective axes 165 and 167 will be either superimposed upon one another, or in parallel with one another and the angle "k" will generally be about zero. In this position, therefore, the cylindrical surfaces 140 will be "matched" or "parallel" with the diamond-shaped surfaces 154 of the respective lateral sides 151 of the respective leaflets 114. The angle "k" is equal to the travel angle "k" when the leaflets are in the fully open position.

Figure 61:
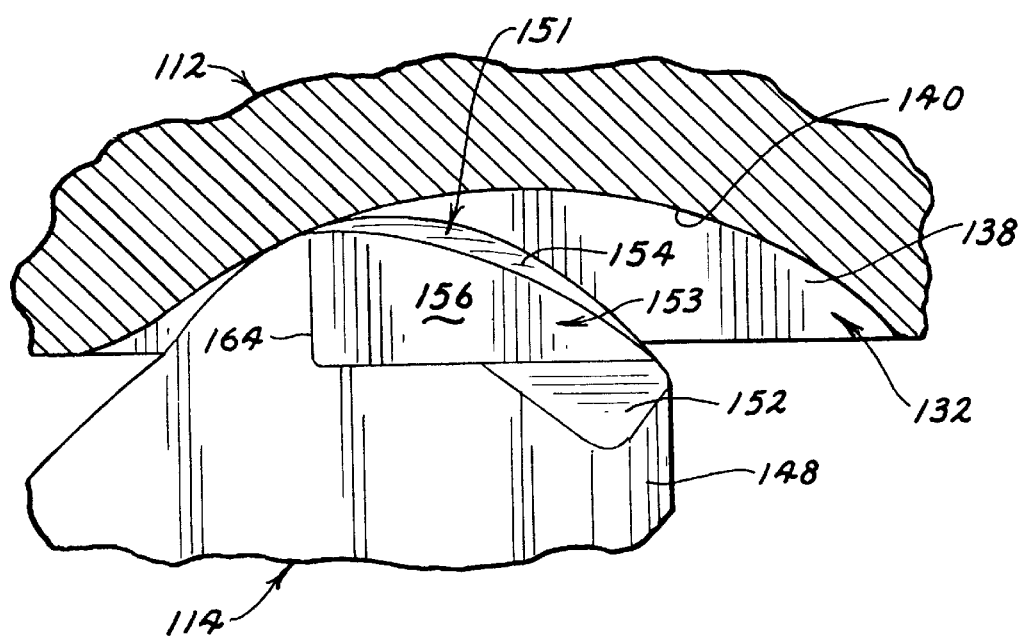
FIG. 61 is a partially broken away cross-sectional view similar to FIG. 60, but showing the leaflet in the fully open position as shown in FIG. 42.

It will be appreciated that significant translational movement is permitted when the leaflets 114 are in the open position. This can be seen in FIG. 56 where the first axis 165 of the leaflet lies at an angle "k" with respect to the second axis 167 of the cylindrical recess bottom surface 140. As shown in FIG. 61, significant room for translational movement is provided. This translational movement of the leaflet 114, when in the fully open position, allows the leaflet 114 to move from its fully open position to its fully closed position much faster than prior art devices. This is because the initial movement, when a retrograde flow of fluid begins, is an upward translational movement of the diamond-shaped surface 154 within the recess 132, until the top side fulcrum edge 166 engages the upper edge sidewall or seat 136 within the recess 132. When the top side fulcrum edge 166 engages the seat 136 within the recess 132, the leaflet 114 has already overcome any inertia it may have had when "resting" in the fully opened position. The translational movement will subsequently give way to pivotal movement of the leaflet toward the fully closed position. This pivotal movement will occur rapidly since the initial translational movement will provide some momentum which will be translated into pivotal or annular movement toward closure of the leaflet 114.

Figure 60:
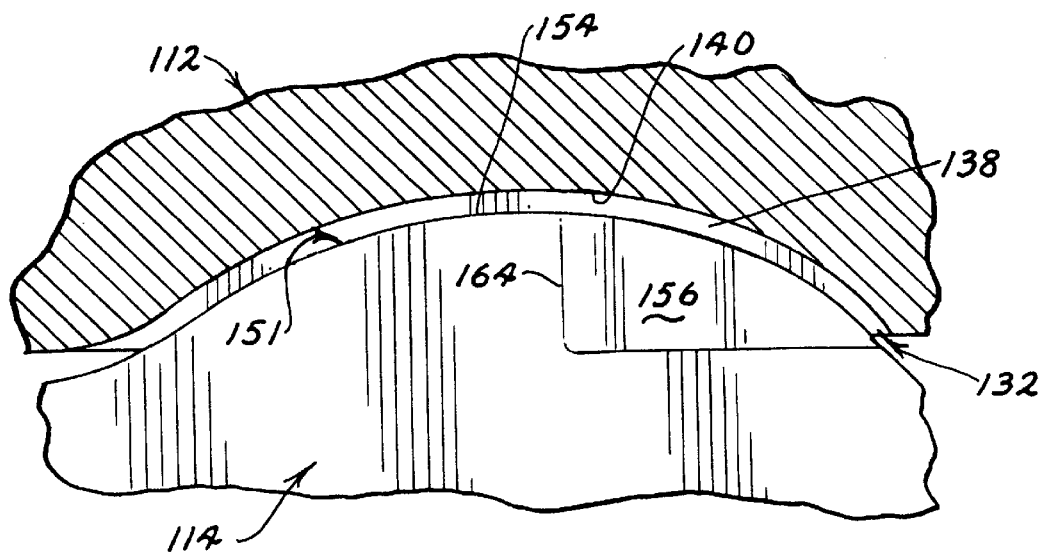
FIG. 60 is a partially broken away cross-sectional view of the recess similar to that shown in FIG. 59 but generally showing a lateral side portion of a leaflet within the recess when the leaflet is in a fully closed position as shown diagrammatically in FIG. 57.

When the leaflet 114 is in the fully closed position, the initial movement of the leaflet is more likely to be followed immediately by a pivotal movement, because the cylindrical diamond-shaped surface 154 and the cylindrical recess bottom surface 140 are more closely mated as shown in FIG. 60 and translational movement from end to end is more limited. The leaflet 114 is likely to slip from the upper side edge 134 toward the lower side sidewall 138, however, because the leaflet will only begin to pivot after the bottom side fulcrum edge 164 is engaged with the lower side sidewall 138. It will be appreciated, however, that the mechanism employed by the respective leaflets for pivoting is still a matter of inquiry and is not fully understood at this time. It is believed, however, that the present pivot mechanism allows for faster opening and closing of the respective valves 110. When the valve is in the open position, and the flow direction changes from antegrade to retrograde, it is believed that the leaflet 114 begins its linear motion immediately with the flow direction and the linear momentum is transferred into angular momentum as soon as the top side fulcrum edge or pivot 166 contacts the side wall 136 proximate the upper edge 134 of the recess 132. This is believed to result in quicker closing than is exhibited by prior art devices. Similarly, from moving from the fully closed position to the fully open position, it is believed that the angular momentum is transferred into linear motion at the end of the leaflet 114 movement, resulting in quicker opening than is possible with the prior art devices.

It is believed that the preferred bileaflet heart valve prosthesis 110 of the present invention provides for a lowered thrombus potential due to the consideration given to access for washing in both the antegrade and retrograde directions. Furthermore, the dynamic pivot mechanism of the preferred leaflets 114 in cooperation with the preferred recesses 132 are believed to provide for faster opening and closing of the valve and less friction in the pivot area due to the use of a "rolling" pivot mechanism wherein the pivot activity changes focus from the top side fulcrum edge 166 to the bottom side fulcrum edge 164. The preferred valve 110 also provides for a minimized travel angle "k'" between the fully opened position and the fully closed position. It is believed that the travel angle provided in the preferred valve 110 may represent at least a 17°–22° reduction in the travel angle as compared to many of the prior art devices. This reduction in the travel angle is believed to minimize angular velocity, wear, cavitation potential, and regurgitation volume, while increasing overall efficiency.

The seats 134 for the preferred leaflets 114 are believed to slow the leaflet 114 just before closure due to the presence of significant amounts of fluids which may be "squeezed" or compressed against the sidewall 126 of the annular base 112. Because the seats slow the leaflet 114 just before closure, they are believed to have a minimizing effect on the cavitation potential. It is also believed that the use of discontinuous seats, or seats which diminish prior to continuing into a seat extending from an opposite recess allows for a slight increase in regurgitation potential proximate the center portion of the leaflet where cavitation potential is generally highest due to the likelihood that this area is likely to be subjected to a greater angular velocity as it comes toward closure against the sidewall 126. The seats 134 also decrease leakage or regurgitation proximate the lateral sides 129 of the annular base 112 when the leaflets 114 are in the closed position. The seats 134 are also believed to provide for increased antegrade flow to wash the flow channels or recesses 132 as the leaflets 114 close. As the leaflets 114 close the fluid in the recesses 132 begins to be "squeezed" or compressed within an upper portion of the recess distal to the transverse sides 131 of the annular base 112. The width of the seats 134 decreases as they extend from the recess 132 to the transverse side 131. Since there is no seat 134 in the center most region of the transverse side 131 in the preferred bileaflet heart valve 110, the fluid "squeezed" or compressed against the seats 134 is generally believed to be released through the bore 116 after it washes at least a portion of the seat 134. While the leaflets 114 are in the closed position, the seats 134 serve to reduce retrograde leakage or regurgitation and at least a portion of the retrograde flow is channeled around the diamond surface 154, so as to thoroughly wash these areas when the leaflets 114 are in a closed position. While the leaflets 114 are in a fully opened position a certain amount of the flow is believed to be channeled between the angular surface 152 of the leaflet 114 and the flow diversion protrusion 130 of the angular base 112. Thus, the lower surface 138 of the recess 132 is thoroughly washed while the leaflets 114 are in the open position.

The bottom surface of the recess 132 is in the form of a curvilinear surface or cylindrical surface and is considered to have a generally cylindrical shape. As used herein, cylindrical surface or cylindrical shape means a surface formed by linear translation of a curve, or a surface which has a radius similar to a portion of a surface of a cylinder. The diamond surface 154 of the leaflets 114 have a cylindrical shape which is "consistent" with or "mates" with the curvilinear or cylindrical recess bottom surfaces 140 of the recesses 132. However, as shown in FIG. 60, the diamond surface 154 is consistent with and mates with the bottom surface 140 of the recess 132 only when the leaflet 114 is in the closed position. However, when the leaflet is in the open position, as shown in FIG. 61, significant room for translational movement is provided. Furthermore, it will be appreciated that the bottom surface of the recess 140 and the matched cylindrical diamond surface 154 of the leaflet 114 will not be in alignment when the leaflet is in any position other than a fully closed position, thus allowing for significant clearance between the extreme edges of the diamond surfaces 154 and the extreme edges of the recesses 132. Because of the increased potential for translational movement when the leaflets 114 are in positions other than the fully closed position, the leaflets 114 will exhibit greater translational freedom for motion than is possible with prior art valves having parallel or matched surfaces in all positions as described and defined in descriptions of the prior art devices.

Figure 56:
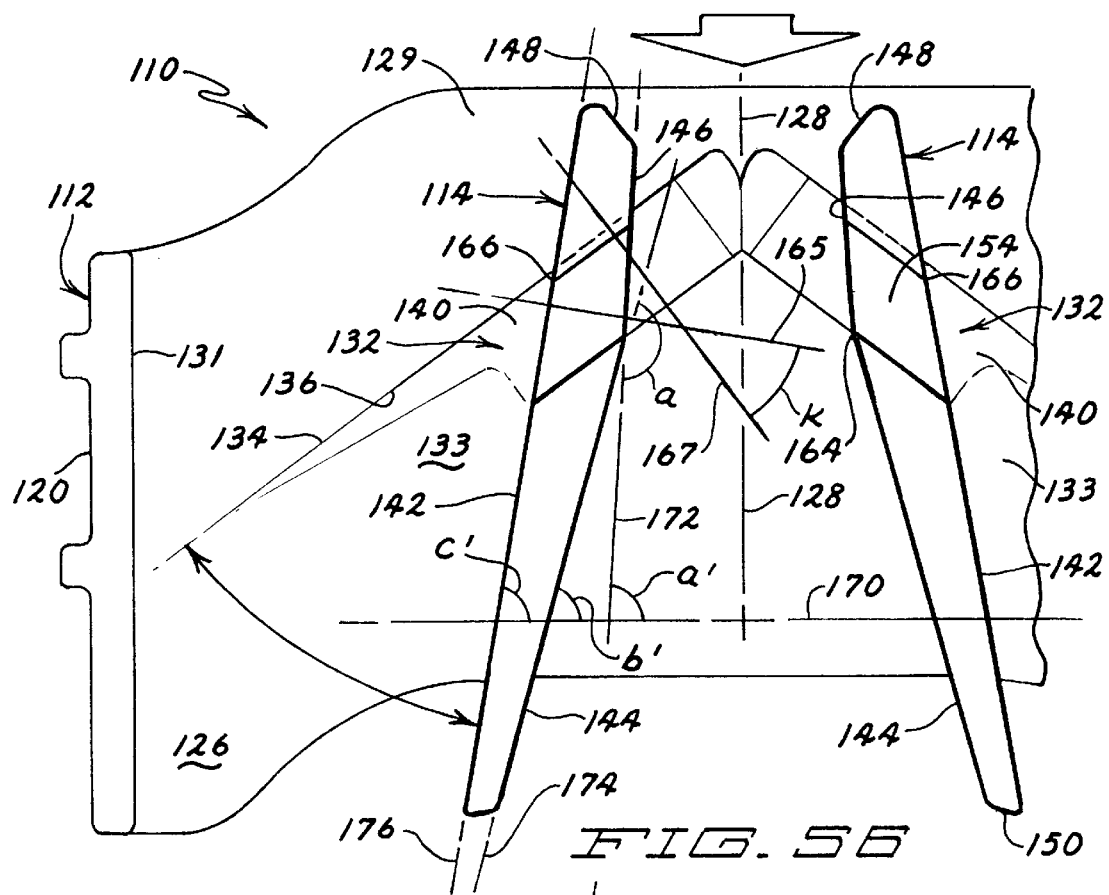
FIG. 56 is a diagrammatic cross-sectional view of the preferred bileaflet heart valve shown in FIG. 42 with the leaflets in a fully open position.

As shown particularly in FIG. 56, the central bevel 146 and the peripheral bevel 144 of the bottom surface of the leaflet each lie generally in a plane respectively designated by tangent lines 172 and 174. As measured by the angle "a" between tangent lines 172 and 174, the peripheral bevel and the central bevel lie generally in planes which lie at an angle to one another. In preferred embodiments this angle will be about 5° to about 16° from 180°, or at an angle of about 164° to about 175°, more preferably about 166° to about 173°. In the most preferred embodiments, the angle "a" will be about 167° to about 172°. In the most preferred working model, the angle "a" is about 169°. This bevel in the leaflet 114, allows the angle of incidence for a flow of blood in the retrograde direction parallel with the longitudinal axis 128 to be a greater angle of incidence in respect to the peripheral bevel 144 than with the central bevel 146. This is believed to be advantageous for at least two reasons. First, since there is a greater angle of incidence, the force of the blood flowing in the retrograde direction will have greater impact upon the leaflet 114 and cause it to pivot toward the fully closed position more rapidly than might otherwise be expected. Furthermore, the difference between the respective bevels, and the angle of the tangent line 176 to the top planar surface 142 allow the peripheral edge 150 to have a shorter radial closing distance to travel before the leaflet 114 is in the fully closed position than might be expected for a leaflet having parallel surfaces.

In preferred embodiments, the angle of the central bevel 146 to a horizontal plane 170, which is consistent with the angle between tangent line 172 and the plane 170, will be an angle "a'". In preferred embodiments, "a'" may range from about 80° to about 97°, preferably about 82° to about 94°, more preferably about 84° to about 88°, and in a most preferred embodiment, "a'" will be about 86°. Similarly, the angle between the peripheral bevel 144 and the horizontal plane 170 may be measured by taking the angle "b'" between the tangent line 174 and the horizontal plane 170. In preferred embodiments, the angle "b'" will be less than 87°, preferably less than 86°. In preferred embodiments, "b'" will range from about 68° to about 84°, preferably about 70° to about 80°, more preferably about 73° to about 77°, and most preferably, it will be about 75°. Similarly, the top planar surface 142 of the top side of the leaflet 114 will lie at an angle "c'" to the horizontal plane 170 as measured between the tangent line 176 and the horizontal plane 170 when the leaflet is in the fully open position. In preferred embodiments, "c'" is greater than about 78° and preferably in a range of from about 80° to about 86°, preferably about 81° to about 83°. In the most preferred embodiment, "c'" is about 81.5°.

Figure 57:
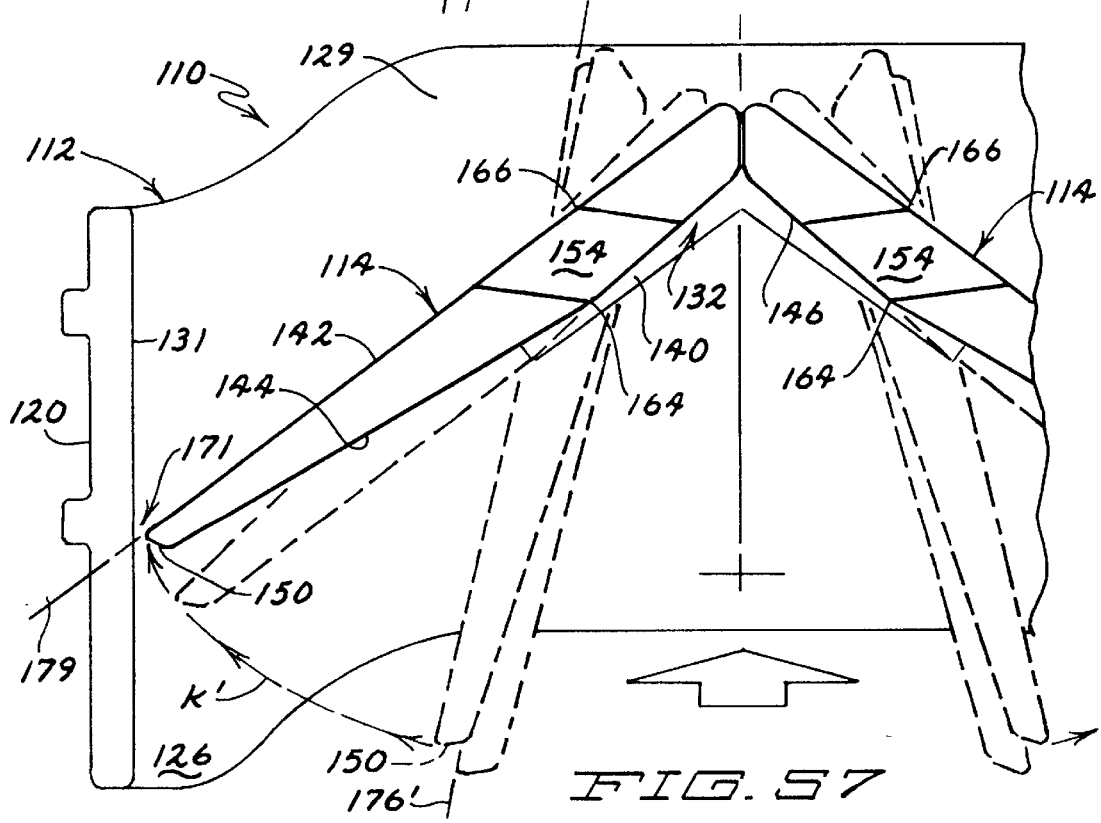
FIG. 57 is a diagrammatic cross-sectional view of the preferred bileaflet heart valve shown in FIG. 42 illustrating the transition of the leaflets from a fully open position to a fully closed position.
Figure 58:
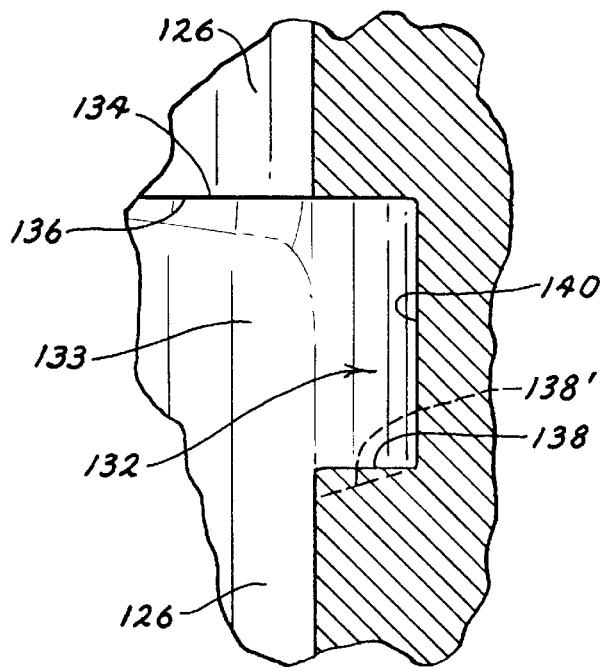
FIG. 58 is a partially broken away cross-sectional view of the recess as seen from the line 58—58 of FIG. 48.

As shown particularly in phantom in FIG. 57, when the leaflet 114 begins to pivot from the fully open position to the fully closed position in response to force exerted upon the peripheral bevel 144, the force can result in an initial translational movement of the leaflet to lift leaflet 114 within the recess 132. When the leaflet 114 has reached the fully closed position shown in FIG. 57, an area on the top planar surface 142 proximate the peripheral edge 150 generally proximate the respective lateral sides 151 will abut against the seat 136 on either lateral side 129 and extend at least partially into the adjacent transverse side 131. When the leaflet 114 is in the fully closed position, the respective mating edges 148 will generally rest against one another while generally allowing at least some retrograde regurgitation of blood between the respective mating surfaces 148.

It will be appreciated that the preferred embodiment of the bileaflet heart valve prosthesis 110 of the present invention will not have any sharp edges and that all edges will in fact be polished, smoothed or feathered so as to minimize shearing of blood as it passes over any of these edges. These smooth "transitions" between surfaces of all kinds will be obtained by shaving and polishing all edges so that the edges are rounded and have a smooth transition from one plane to another. Any radial surfaces of course will be polished as well.

As shown in FIG. 64, the amount of regurgitation of blood in the retrograde direction is relatively significant. Heart valves are generally designed with at least some regurgitation in mind so long as the regurgitation does not reduce the efficiency of the heart. It is believed that the regurgitation is important to permit the washing of the various surfaces of the present prosthetic device. FIG. 66 generally provides a representation of the quantity (Q) of blood flowing through a bileaflet heart valve during a contraction cycle when the valve is in the aortic position. During systole, the quantity of blood passing through the valve in the antegrade direction (+) is fairly significant. As the force from the contraction diminishes from its highest point, indicated at the apex of the curve (Qsys), until the antegrade flow ends and blood begins to flow in the retrograde direction (−), the leaflets 114 remain in an open position. The retrograde flow then begins to push the leaflets 114 toward the closed position at the lowest point of the curve below the "y" axis (Qcl). As the leaflets 114 close, most of the retrograde flow is obstructed, but not all of it. The remaining retrograde flow is due to leakage around the leaflets 114. The retrograde leakage (Ql) has been discussed herein and is believed to have a positive effect in respect to washing the various surfaces of the prosthetic heart valve, in that this "regurgitation" will "wash" the surfaces to reduce stagnation of blood as a measure against potential thrombus.

Figure 47:
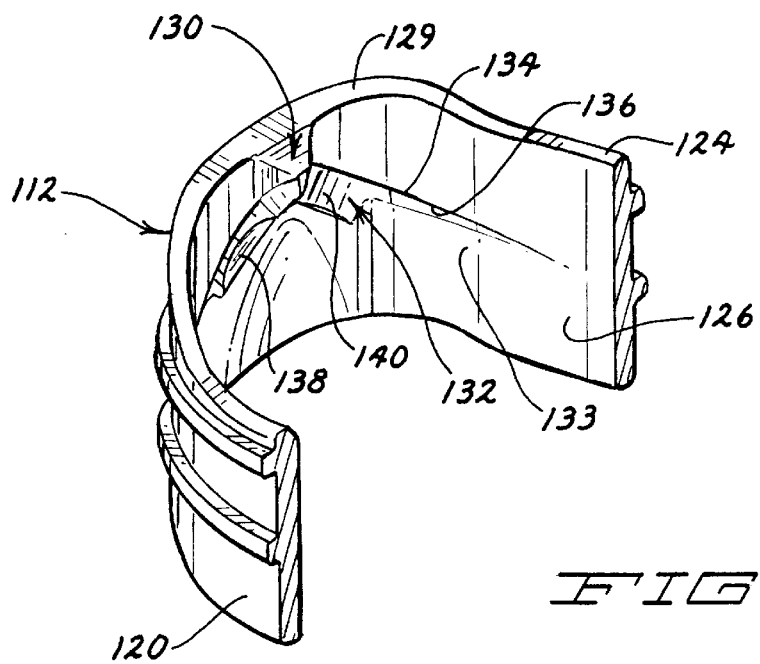
FIG. 47 is a partially broken away elevated perspective view of the annular base of the preferred bileaflet heart valve shown in FIG. 42.
Figure 48:
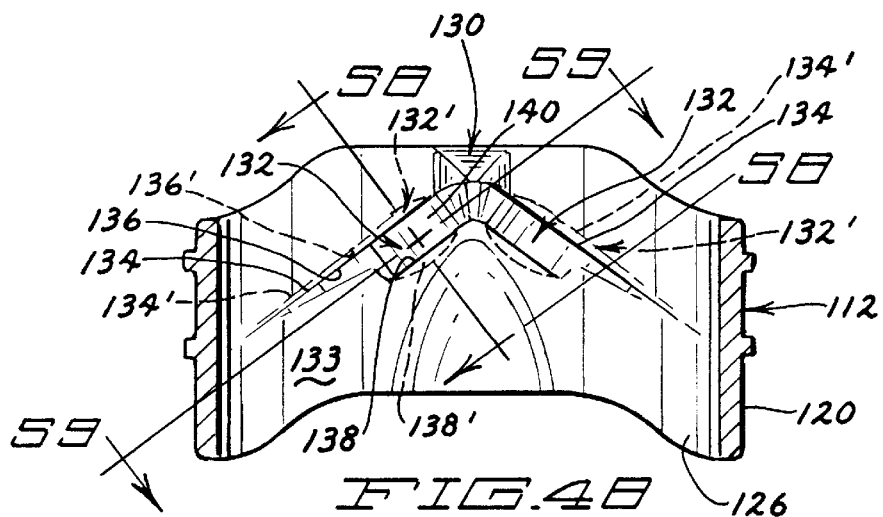
FIG. 48 is a cross-sectional lateral view of the annular base of the preferred bileaflet heart valve shown in FIG. 42.
Figure 49:
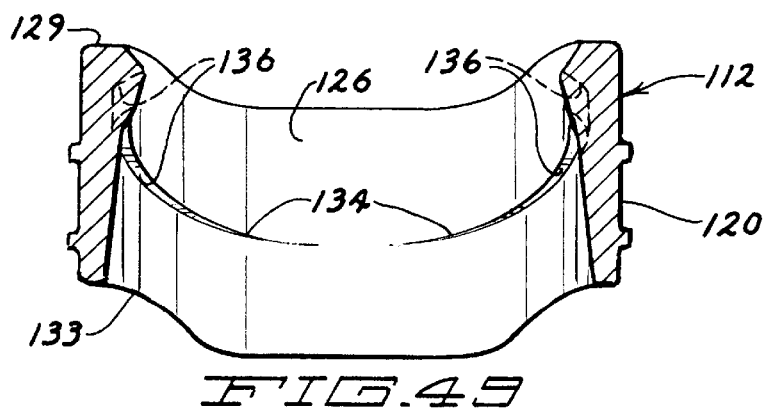
FIG. 49 is a lateral side cross-sectional view of the annular base of the preferred bileaflet heart valve shown in FIG. 42.
Figure 50:
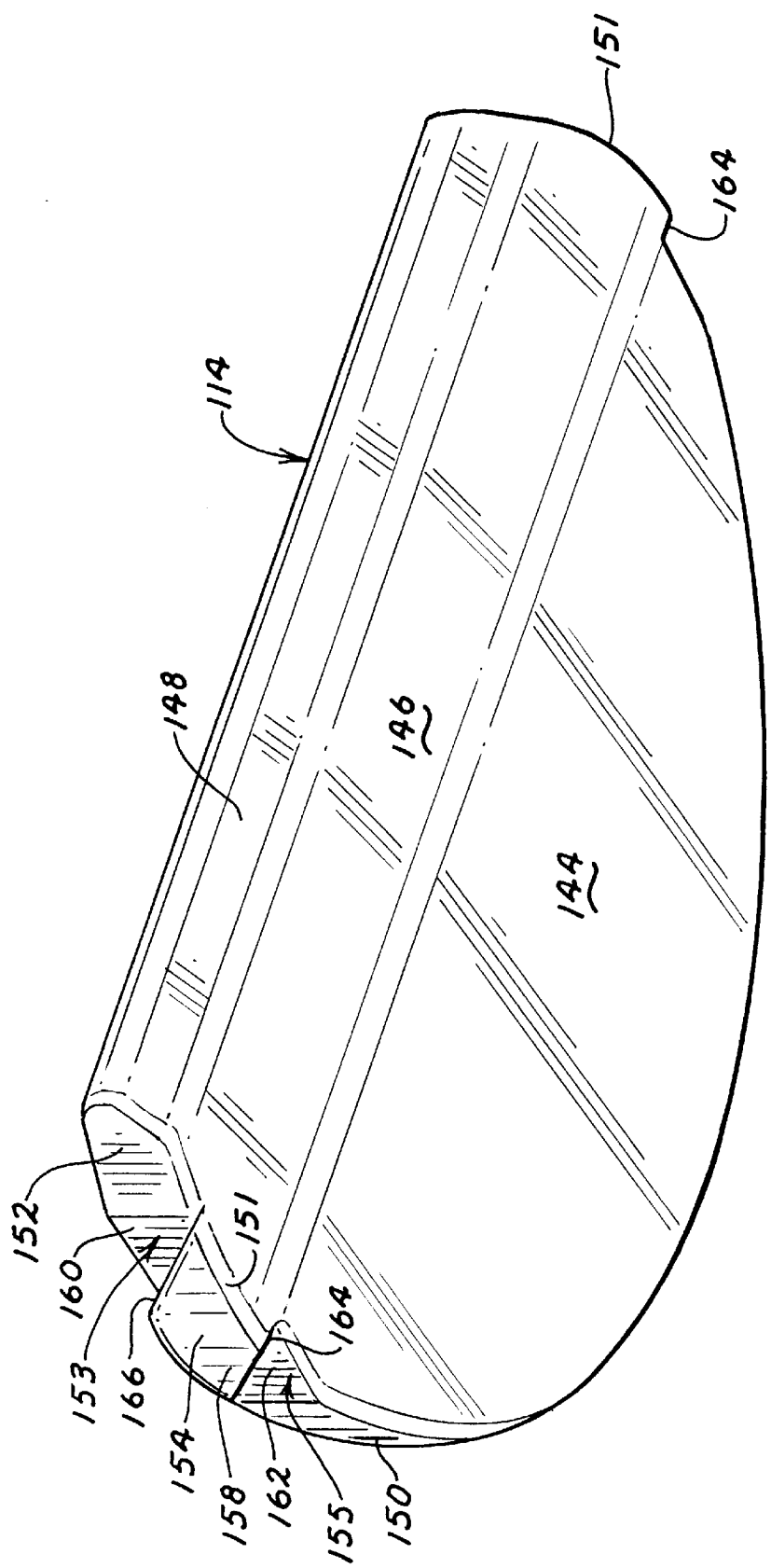
FIG. 50 is an elevated perspective view of the bottom side of the preferred leaflet shown in FIG. 42.
Figure 51A:
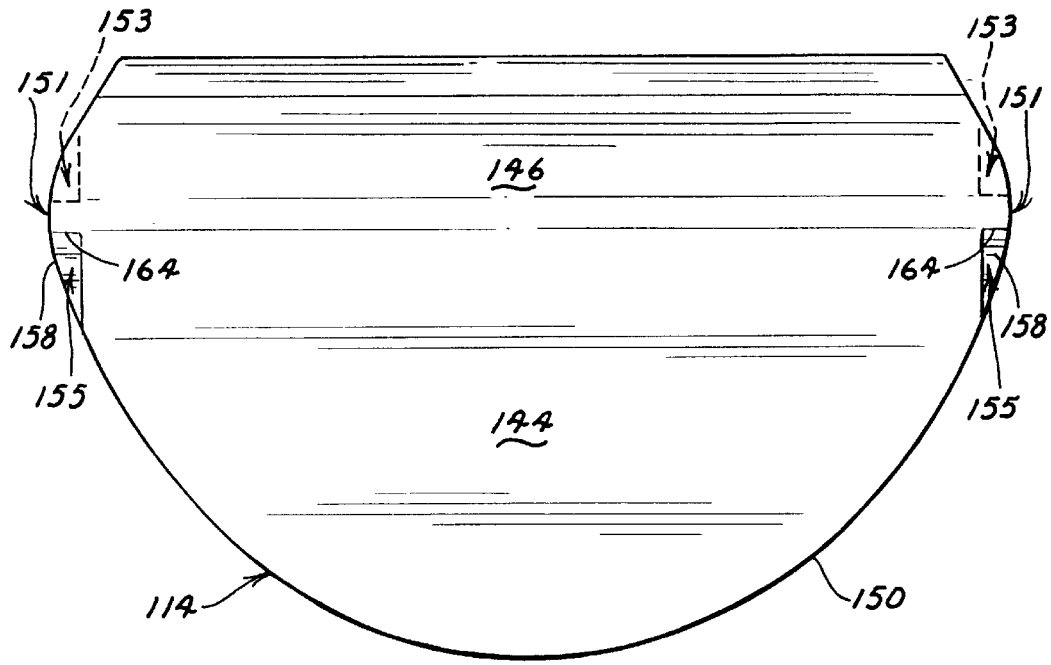
FIG. 51A is a bottom plan view of a leaflet of the preferred bileaflet heart valve shown in FIG. 42.
Figure 51B:
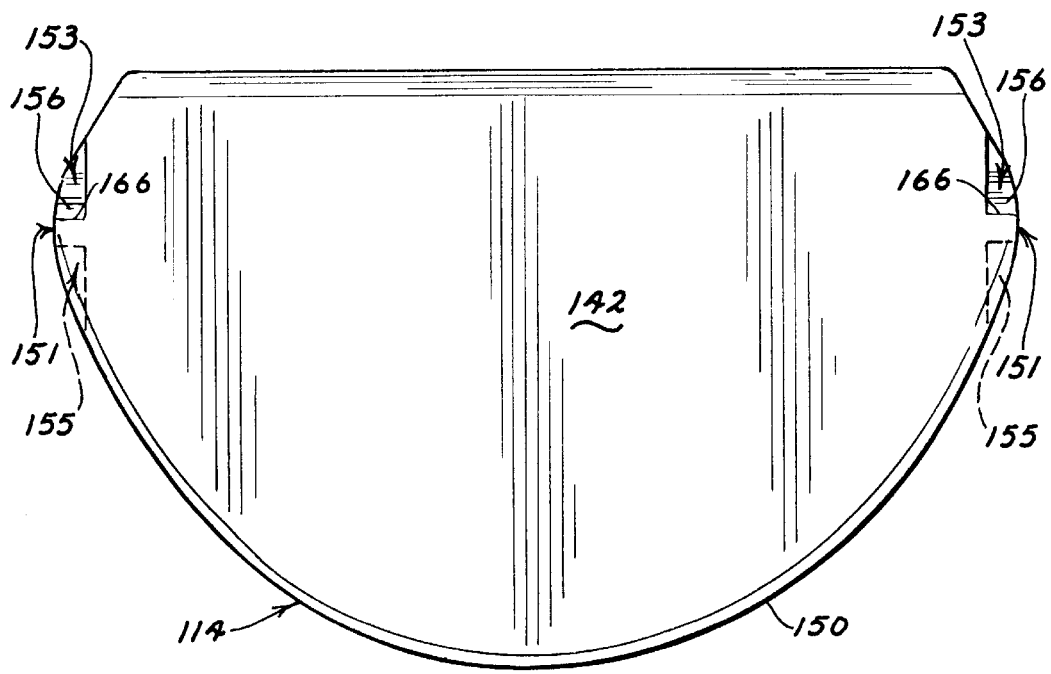
FIG. 51B is a top plan view of a leaflet of the preferred bileaflet heart valve shown in FIG. 42.
Figure 65:
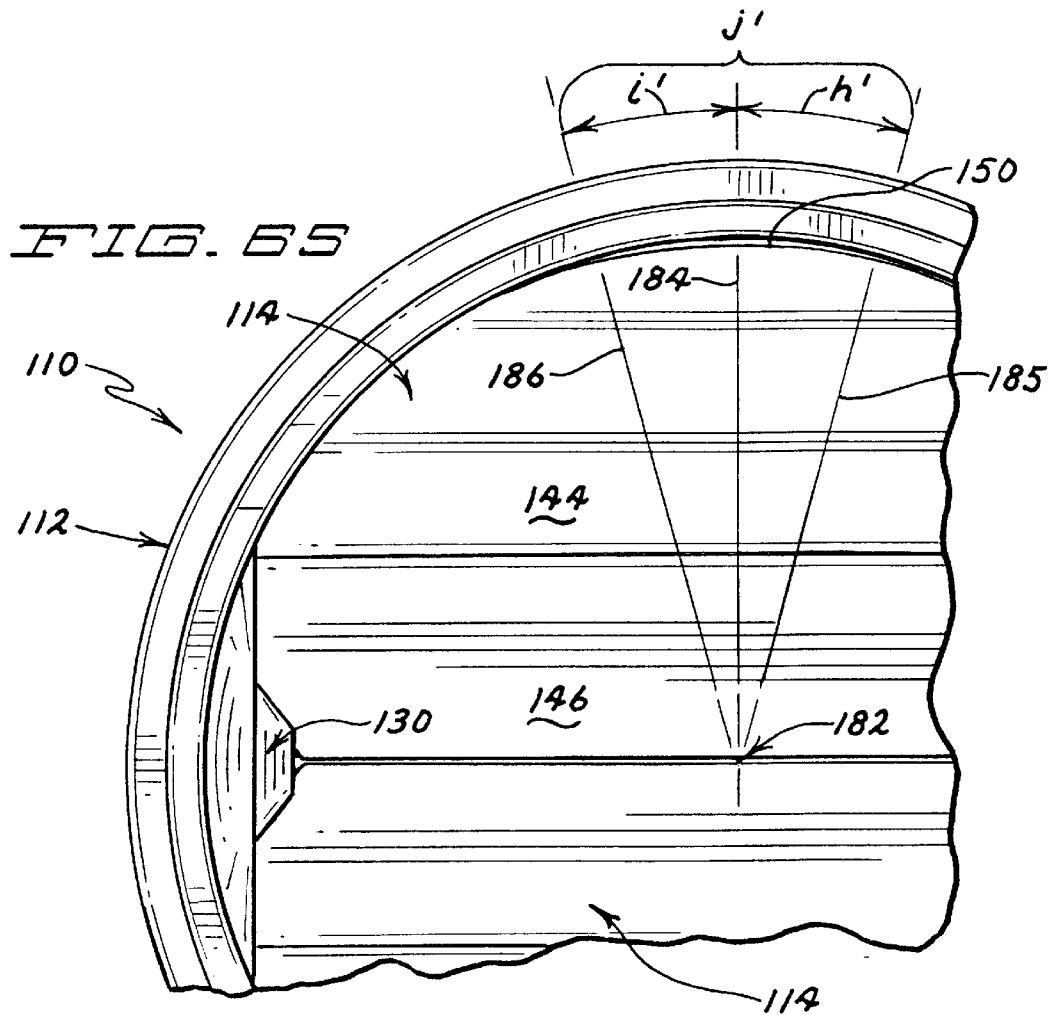
FIG. 65 is a partially broken away bottom plan view of the preferred bileaflet heart valve shown in FIG. 64 when the leaflets are in a fully closed position.

As shown particularly in FIGS. 47 and 49 and demonstrated diagrammatically in FIG. 65, the upper edge 134 blends or "feathers" into the inner wall 126 of the annular base 112, as does the seat 136, in preferred embodiments. It is believed that this has a very positive effect upon preservation of the integrity of the top planar surface 142 of the respective leaflets 114 by reducing cavitation potential. This is particularly true in an area approximately 15° to either side of a center line 184 bisecting a leaflet 114, and in the areas most proximate to the peripheral edge 150. The potential for negative effects of cavitation upon the top planar surface 142 is also reduced by the shortened travel angle "k'" between the location of the top planar surface 142 when the leaflet is in the fully open position, and the top planar surface 142 when the leaflet is in the fully closed position as represented by tangent line 179 of FIG. 57. Because the preferred leaflet 114 of the present invention has a "double-beveled" bottom surface, the position of the top planar surface 142 in relation to the side wall 126 can be minimized to reduce the radial distance "k'" traveled by the top planar surface 142 in moving to the closed position. In this way, the angular speed of the movement of the most distal portion of the top planar surface 142 proximate the peripheral edge 150, where the cavitation potential is generally believed to be the greatest, is diminished gradually when the leaflet 114 approaches the closed position. Cavitation potential is also minimized because the distance is minimized by the beveled design of the leaflets 114. In this regard, it will be appreciated that the leaflet will continue to gain speed as it pivots through a greater radial distance. Therefore, by minimizing the radial distance between the open position and the closed position, the radial speed of the leaflet 114 can be minimized. In preferred embodiments, the travel angle "k'" will be from about 30° to about 55°, preferably about 33° to about 52°, more preferably about 34° to about 50°, even more preferably about 35° to about 49°, even more preferably about 37° to about 47°, and most preferably about 40° to about 45°. Cavitation potential is also reduced because the seats 136, extending from the respective recesses 132 on the respective lateral sides of the leaflet 114, help to slow the closure or "cushion" the closure of the leaflet against the side wall 126 because the blood between the peripheral edge 150 and the proximate portions of the top planar surface 142 must be "squeezed" out of the intervening space adjacent the respective seat 136 as the leaflet 114 is pivoting toward the fully closed position.

Furthermore, the gap 171 permits a continuing flow of blood in the retrograde direction which also helps to prevent the formation of a vacuum on the top planar surface 142 proximate the peripheral edge 150 which is generally the genesis of cavitation damage on the planar surfaces of a leaflet 114. The "cushioning" effect of the partial or "discontinuous" seats 136 also helps to prevent stress to other portions of the leaflet 114 as they collide with the side wall 126 or the seat 136.

In FIG. 65, a center line 184 extending from a center point 182 is shown superimposed upon a bottom surface of a leaflet 114. In preferred embodiments, the respective seats 136 extending from respective recesses 132 will extend only as far as the radius lines 185 and 186 which are radially equidistance from the center line 184. For this reason, the radial angle "i'" will equal the radial angle "h'" between the radius lines 186, 185 and the center line 184, respectively, and the radial angle "j'" will equal twice either of the equal angles "i'" and "h'". In preferred embodiments, the radial angle of "j'" will range from about 5° to about 55°, preferably about 10° to about 30°. The reason for limiting the extension of the seats 136 entirely through the inner wall 126 proximate the transverse surface 131 is in part because of a desire to minimize the cavitation potential which is generally greatest within 15° on either side of a center line 184 bisecting the top planar surface 142 of a pivotal leaflet 114 of a bileaflet heart valve. It will be understood that the area having the greatest cavitation potential is likely to be at the most distal portion of the top planar surface 142 from the center point 182, because it is this portion of the leaflet 114 which gains the most angular speed when the leaflet is pivoting toward closure and is most capable of generating the force required to create cavitation bubbles on the top planar surface 142. Therefore, eliminating the seat 136 in this particular area, is expected to minimize cavitation potential by permitting more regurgitation through the gap 171.

Referring now to FIGS. 62 and 63, the recesses 132 of the preferred valve 110 may be varied in the manner shown diagrammatically in these figures. The alternate leaflets "114'" and "144''" are shown in FIGS. 62 and 63, respectively. FIG. 62 shows recesses "132'" which have no seat or extension and they are turned radially from the position of the recesses 132 shown in FIG. 48. The recesses "132''" shown in FIG. 63 have been turned an intermediate amount. In each case, it will be appreciated that the respective cylindrical diamond-shape surface "154'", "154''" will be reoriented on the respective lateral sides "151'", "151''" of the respective leaflets "114'", "11''" in order to accommodate the different planes occupied by the upper and lower side walls of the alternate recesses "132'", "132'". The overall mechanism has not changed from that discussed previously in relation to FIGS. 48 and 56–57. In each case, the respective recesses "132'", "132''" permit some translational movement in the direction of the respective ends of the respective recesses "132'", "132''" when the respective leaflets are in the open position, until the respective top side fulcrum edge "166'","166''" engages the respective upper side side wall "136'", "136''". When the respective alternate leaflets "114'", "114 ''" are in the fully closed position, it is believed that translational movement at the beginning the antegrade flow cycle will be primarily limited to a "sideways" shifting of the respective diamond-shape surface "154'", "154''" until the respective bottom side fulcrum edge "164'", "164''" engages the respective lower side wall "138'", "138''", and the respective leaflet "114'", "114''" begins to pivot on the respective fulcrum edge "164'", "164''". As the respective leaflet gradually pivots to the fully open position, greater translational movement is permitted as is discussed elsewhere in this disclosure.

While the preferred embodiments of the above bileaflet heart valve 10, 110 have been described in detail with reference to the attached drawings, it will be understood that various changes and adaptations may be made in the bileaflet heart valve 10, 110 without departing from the spirit and scope of the appended claims. It is to be understood that even though numerous characteristics and advantages of various embodiments of the present invention have been set forth in the foregoing description, together with details of the structure and function of various embodiments of the invention, this disclosure is illustrative only and changes may be made in detail, especially in matters of shape, size and arrangement of parts, within the principles of the present invention, to the full extent indicated by the broad general meaning of the terms in which the appended claims are expressed.

What is claimed is:

1. A bileaflet heart valve prosthesis for controlling a circulation of a fluid within a heart of a patient, said bileaflet heart valve prosthesis having:

an annular base and first and second leaflets, the first and second leaflets each being separately mounted within the annular base for pivotal movement between a closed position and an open position, the annular base defining a bore extending through the base, the annular base having a first lateral side having a first lateral surface, a second lateral side having a second lateral surface, and a pair of transverse sides having respective transverse surfaces individually disposed between the first and second lateral surfaces, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, wherein at least a portion of the first leaflet is received within the first recess and at least a portion of the first leaflet is received within said second recess to retain the first leaflet within the annular base, wherein the annular base further defines third and fourth recesses extending radially outward into the annular base from and communicating with the bore, the third recess being disposed within the first lateral side and the fourth recess being disposed within the second lateral side, wherein at least a portion of the second leaflet is received within the third recess and at least a portion of the second leaflet is received with the fourth recess to retain the second leaflet within the annular base; wherein each leaflet has an upper surface and a curved peripheral edge and each recess has a bottom surface and an upper side and a lower side, the upper side and the lower side respectively defining upper and lower edges of the bottom surface, the upper side extending from the respective recess proximate the respective lateral side to a location on an adjacent transverse side, the upper edge of each recess forming a seat against which an area on the upper surface, proximate the curved peripheral edge of a leaflet engaged within the respective recess, can abut when the leaflet is in the closed position, the improvement characterized in that each of the respective upper edges forms a seat which extends from one recess generally toward another and diminishes to become a smooth surface which is flush with the respective transverse surface.

2. The bileaflet heart valve prosthesis of claim 1, wherein each upper side has an end point where the seat diminishes into the respective transverse surface and no longer provides a seat against which the upper surface proximate the peripheral edge can abut, wherein the annular base has an inner surface which includes each of the lateral surfaces and the transverse surfaces, the annular base having a radial distance which extends 360° around the inner surface, wherein the upper side extending from the first recess is the first upper side and the upper side extending from the second recess is the second upper side and the radial distance between the respective end points of the first and second upper sides is from about 5° to about 55°.

3. A bileaflet heart valve prosthesis for controlling a circulation of a fluid within a heart of a patient, said bileaflet heart valve prosthesis comprising an annular base and first and second leaflets, the first leaflet and the second leaflet being mounted within the annular base for pivotal movement between a fully closed position and a fully open position, the annular base defining a bore extending through the base, the annular base having a first lateral side having a first lateral surface, a second lateral side having a second lateral surface, and a pair of transverse sides individually disposed between the first and second lateral sides, wherein each of the respective leaflets have first and second sides, the first side being a top side and the second side being a bottom side, the bottom sides of the respective leaflets generally facing one another when the respective leaflets are in the fully open position; and wherein each bottom side is substantially defined by an upper surface lying generally in a first plane and a lower surface lying generally in a second plane, the first plane lying at an angle to the second plane; and the top sides of the respective leaflets having a top surface lying generally in a third plane, the third plane lying at an angle to each of the first and second planes.

4. The bileaflet heart valve prosthesis of claim 3, wherein the first and second planes lie at first and second angles respectively to a horizontal plane passing through a cross-section of the annular base when the respective leaflets are in the fully open position, the first angle being from about 84° to about 88° and the second angle being from about 68° to about 84°.

5. The bileaflet heart valve prosthesis of claim 3, wherein the angle between the first plane and the second plane is from about 164° to about 175°.

6. The bileaflet heart valve prosthesis of claim 3, wherein each of the top planes changes position from a first position to a second position when the respective leaflet changes position from the fully open position to the fully closed position, wherein a travel angle is an angle between the respective top plane when the leaflet is in the first position and the respective top plane when the leaflet is in the second position, and wherein the travel angle for each of the first and second leaflets is from about 35° to about 49°.

7. The bileaflet heart valve prosthesis of claim 6, wherein a horizontal plane, which is perpendicular to the lateral sides of the annular base, passes through a horizontal cross-section of the base, and each of the respective top planes lie at a greater angle to the horizontal plane than the second plane on the respective lower surface.

8. The bileaflet heart valve prosthesis of claim 3, wherein a horizontal plane, which is perpendicular to the lateral sides of the annular base, passes through a horizontal cross-section of the base, and the second plane lies at an angle to the horizontal plane when the respective leaflet is in the fully open position, the angle ranging from about 68° to about 84°.

9. A bileaflet heart valve prosthesis for controlling a circulation of a fluid within a heart of a patient, said bileaflet heart valve prosthesis having:

an annular base and first and second leaflets, the first leaflet and the second leaflet being mounted within the annular base for pivotal movement between a fully closed position and a fully open position, the annular base defining a bore extending through the base, the annular base having a first lateral side having a first lateral surface, a second lateral side having a second lateral surface, and a pair of transverse sides individually disposed between the first and second lateral sides, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, wherein at least a first side portion of the first leaflet is received within the first recess and at least a second side portion of the first leaflet is received within said second recess to retain the first leaflet within the annular base, wherein the annular base further defines third and fourth recesses extending radially outward into the annular base from and communicating with the bore, the third recess being disposed within the first lateral side and the fourth recess being disposed within the second lateral side, wherein at least a third side portion of the second leaflet is received within the third recess and at least a fourth side portion of the second leaflet is received within the fourth recess to retain the second leaflet within the annular base; the improvement characterized in that the first, second, third and fourth side portions of the respective leaflets each have a plurality of recess engagement surfaces, two of the plurality of recess engagement surfaces meeting to form a first fulcrum edge and two of the plurality of recess engagement surfaces meeting to form a second fulcrum edge removed from the first fulcrum edge, each of the recesses having an upper and lower recess side surface, wherein each of the respective first and second fulcrum edges engage an upper or lower recess side surface of the recess in which the respective side portion is engaged when the respective leaflet pivots either from the fully open position to the fully closed position or from the fully closed position to the fully open position such that engagement between one of the respective fulcrum edges and the respective side surface of each of the respective recesses is changeable from engagement with a side surface by the first fulcrum edge to engagement with a side surface by the second fulcrum edge as the respective leaflet pivots from one position to the other; each recess having a recess bottom surface, wherein at least a portion of each recess bottom surface is a cylindrical surface; the first leaflet having a peripheral edge, wherein the respective side portions of the first leaflet, which are received within the first and second recesses, each have a cylindrical surface along the peripheral edge proximate the respective side portions received within the respective recesses; the first leaflet having a complementary pair of notches in the peripheral edge proximate each of the respective side portions of the first leaflet which are received within the respective first and second recesses, wherein the complementary pair of notches cooperate to permit the leaflet to pivot within the respective recess and the cylindrical surfaces of the respective peripheral edges mate with the cylindrical bottom surfaces of the respective recesses in which the respective side portions are received when the first leaflet is in the closed position.

10. The bileaflet heart valve prosthesis of claim 9, each of the respective leaflets having first and second sides, the first side being a top side and the second side being a bottom side, the bottom sides of the respective leaflets generally facing one another when the respective leaflets are in an open position; each bottom side having an upper surface lying generally in a first plane and a lower surface lying generally in a second plane, the first plane lying at an angle to the second plane.

11. The bileaflet heart valve prosthesis of claim 9, each of the respective side portions of the respective leaflets having a cylindrical side surface along a peripheral edge of the leaflet proximate the respective side portion which is received within the respective recess, wherein the respective cylindrical side surfaces mate with the respective cylindrical bottom surfaces of the respective recesses in which the respective side portions are received when the respective leaflets are in the closed position.

12. A bileaflet heart valve prosthesis for controlling a circulation of a fluid within a heart of a patient, said bileaflet heart valve prosthesis having:

an annular base and first and second leaflets, the first leaflet and the second leaflet being separately mounted within the annular base for pivotal movement between a closed position and an open position, the annular base defining a bore extending through the base, the base having a longitudinal axis oriented generally in parallel with the bore, the annular base having a first lateral side having a first lateral surface, a second lateral side having a second lateral surface, and a pair of transverse sides individually disposed between the first and second lateral sides, the annular base defining a first recess extending radially outward into the annular base from and communicating with the bore, and a second recess extending radially outward into the annular base from and communicating with the bore, the first recess being disposed within the first lateral side, the second recess being disposed within the second lateral side, the first recess having a first recess surface, the first recess surface intersecting the first lateral surface of the base such that the first recess surface and the first lateral surface form a first junction, a first recess entrance angle being the largest of a plurality of angles between a first line tangential with the first lateral surface proximate the first junction and any of an infinite number of second lines lying in a first plane with and intersecting the first line, and being generally tangential with any portion of the first recess surface proximate the first junction, the first plane being perpendicular to the first lateral surface, the second recess having a second recess surface intersecting the second lateral surface such that the second recess surface and the second lateral surface form a second junction, a second recess entrance angle being the largest of a plurality of angles between a third line tangential with the second lateral surface proximate the second junction and any of an infinite number of fourth lines lying in a second plane with and intersecting the third line, and being generally and tangential with any portion of the second recess surface proximate the second junction, the second plane being perpendicular to the second lateral surface; wherein at least a first side portion of the first leaflet is received within the first recess and at least a second side portion of the first leaflet is received within the second recess to retain the first leaflet within the annular base; the improvement characterized in that each of the first and second recess entrance angles are less than about 35°; wherein at least a portion of each of the first and second recess surfaces is a cylindrical surface; the first leaflet having a peripheral edge, wherein the respective side portions of the first leaflet, which are received within the first and second recesses, each have a cylindrical surface along the peripheral edge proximate the respective side portions received within the respective recesses; the first leaflet having a complementary pair of notches in the peripheral edge proximate each of the respective side portions of the first leaflet which are received within the respective first and second recesses, wherein the complementary pair of notches cooperate to permit the leaflet to pivot within the respective recess and the cylindrical surfaces of the respective peripheral edges mate with the cylindrical surfaces of the respective recesses in which the respective side portions are received when the first leaflet is in the closed position.

13. The bileaflet heart valve prosthesis of claim 12 wherein the first and second recess entrance angles range from about 20° and about 34°.

14. The bileaflet heart valve prosthesis of claim 12, wherein the annular base further defines third and fourth recesses extending radially outward into the annular base from and communicating with the bore, the third recess being disposed within the first lateral side and the fourth recess being disposed within the second lateral side, the third recess having a third recess surface intersecting the first lateral surface such that the third recess surface and the first lateral surface form a third junction, a third recess entrance angle being the largest of a plurality of angles between a fifth line generally tangential with the first lateral surface proximate the third junction and any of an infinite number of sixth lines lying in a third plane with and intersecting the fifth line, and being generally tangential with any portion of said third recess surface proximate the third junction, the third plane being perpendicular to the first lateral surface, the fourth recess having a fourth recess surface intersecting the second lateral surface, the fourth recess surface and the second lateral surface intersecting to form a fourth junction, a fourth recess entrance angle being the largest of a plurality of angles between a seventh line tangential with the second lateral surface proximate the fourth junction and any of an infinite number of eighth lines lying in a fourth plane with and intersecting the seventh line, and being generally tangential with any portion of the fourth recess surface proximate the fourth junction, the fourth plane being perpendicular to the second lateral surface; each of the third and fourth recess entrance angles being less than about 35°, wherein at least a third side portion of the second leaflet is received within the third recess and at least a fourth side portion of the second leaflet is received with the fourth recess to retain the second leaflet within the annular base.

15. The bileaflet heart valve prosthesis of claim 12, wherein the first leaflet has first and second sides, the first side being the top side and the second side being the bottom side, the bottom side having an upper surface lying generally in a first plane and a lower surface lying generally in a second plane, the first plane lying at an angle to the second plane.

* * * * *